US012728187B2

(12) United States Patent
Xie et al.

(10) Patent No.: US 12,728,187 B2
(45) **Date of Patent: *Sep. 8, 2026**

(54) BREAST PUMP DEVICE, BREAST PUMP SYSTEM, AND METHOD FOR OPERATING THE SAME

(71) Applicant: SHENZHEN LUTE JIACHENG SUPPLY CHAIN MANAGEMENT CO., LTD., Shenzhen (CN)

(72) Inventors: Guangbao Xie, Shenzhen (CN); Wanyuan Chen, Shenzhen (CN); Yangyang Hu, Shenzhen (CN)

(73) Assignee: SHENZHEN LUTE JIACHENG SUPPLY CHAIN MANAGEMENT CO., LTD., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/339,252

(22) Filed: Sep. 24, 2025

(65) Prior Publication Data

US 2026/0021226 A1 Jan. 22, 2026

Related U.S. Application Data

(63) Continuation of application No. 18/770,644, filed on Jul. 11, 2024, now Pat. No. 12,440,611, which is a continuation of application No. PCT/CN2023/143316, filed on Dec. 29, 2023.

(51) Int. Cl.
*A61M 1/06* (2006.01)

(52) U.S. Cl.
CPC ............ *A61M 1/066* (2014.02); *A61M 1/067* (2021.05); *A61M 2205/8206* (2013.01)

(58) Field of Classification Search
CPC ............................................ A61M 1/06–0697
See application file for complete search history.

(56) References Cited

U.S. PATENT DOCUMENTS

2009/0156990 A1* 6/2009 Wenger .................. G06F 16/60 604/67
2017/0072118 A1* 3/2017 Makower ............. A61M 1/067
2018/0333523 A1* 11/2018 Chang ............... A61M 1/06935
2022/0257858 A1* 8/2022 Grosman ............ A61M 5/1723

* cited by examiner

*Primary Examiner* — Courtney Fredrickson
(74) *Attorney, Agent, or Firm* — BAYES PLLC

(57) ABSTRACT

A breast pump device is disclosed. The breast pump device includes a primary machine portion, and a secondary control portion without any pump. The secondary control portion is provided separately from the primary machine portion. The primary machine portion further includes a main housing, a pump attached to the main housing and configured to generate a pressure to cause breast milk to be expressed by a user of the breast pump device, and a milk container coupled to the pump and configured to accommodate the breast milk. The secondary control portion is electrically coupled to the primary machine portion and configured to remotely operate the primary machine portion. The primary machine portion is configured to be worn on a breast of the user during operation. The secondary control portion is integrated into a wearable device configured to be worn on the neck or head of the user.

19 Claims, 21 Drawing Sheets

212

501

BREAST PUMP DEVICE, BREAST PUMP SYSTEM, AND METHOD FOR OPERATING THE SAME

CROSS-REFERENCE TO RELATED APPLICATIONS

The present application is a continuation of U.S. application Ser. No. 18/770,644, filed on Jul. 11, 2024, which is a continuation of International Application No. PCT/CN2023/143316, filed on Dec. 29, 2023. The contents of these applications are incorporated herein by reference in their entireties.

BACKGROUND

The present disclosure relates to a breast pump device, a breast pump system, and a method for operating the same, in particular to a portable breast pump device with two electrically coupled portions.

Breast pump devices are innovative gadgets that help nursing mothers express milk in traditionally unavailable environments. For example, in the past, nursing mothers at work or school had to stay in private spaces to express milk, and they could not express milk while walking or traveling on public transport. This inconvenience not only hampers their ability to feed babies, but may also cause health problems, such as breast engorgement.

The advent of breast pump devices frees nursing mothers from such mental and physical discomfort. A breast pump device creates suction on a breast of a mother, mimicking that of a newborn, so that milk is expressed from the breast and collected by a container of the device. The suction in these devices is generated by an air pump, and transmitted to the breast via an intermediate conduit. However, due to its large size, the pump in the existing art is provided separately from other components, and not in proximity to the user. Thus, an air line or a tube is needed as an airway between the separate pump and the other components. This brings new problems. Due to its unpliant material and large diameters, the air line or the tube cannot be easily bent and stored when the breast pump device is not in use, and can obstruct the airway between the pump and the other components when twisted or bent while in use, thus causing malfunction of the breast pump device. Moreover, the size of the pump makes it hard to be concealed, adding awkwardness to the user in public. Therefore, improvements to the existing breast pump devices become necessary.

SUMMARY

In one aspect, a breast pump device includes a primary machine portion, and a secondary control portion without any pump. The secondary control portion is provided separately from the primary machine portion. The primary machine portion further includes a main housing, a pump attached to the main housing and configured to generate a pressure to cause breast milk to be expressed by a user of the breast pump device, and a milk container coupled to the pump and configured to accommodate the breast milk. The secondary control portion is electrically coupled to the primary machine portion and configured to remotely operate the primary machine portion. The primary machine portion is configured to be worn on a breast of the user during operation. The secondary control portion is integrated into a wearable device configured to be worn on the neck or head of the user.

In another aspect, a breast pump system includes two primary machine portions. At least one of the primary machine portions includes a main housing, a pump attached to the main housing and configured to generate a pressure to cause breast milk to be expressed by a user of the breast pump system, and a milk container coupled to the pump and configured to accommodate the breast milk. The breast pump system further includes a secondary control portion provided separately from the primary machine portions. The secondary control portion is electrically coupled to at least one primary machine portion by wire and configured to remotely operate two primary machine portions. The two primary machine portions are each configured to be worn on a breast of the user during operation, and the secondary control portion is configured to be worn on the neck or head of the user.

In still another aspect, a method for operating a breast pump device having a first primary machine portion and a secondary control portion includes separately providing the first primary machine portion and the secondary control portion, electrically coupling the first primary machine portion and the secondary control portion by wire, and remotely operating the first primary machine portion by the secondary control portion to generate a pressure within the first primary machine portion that causes breast milk to be expressed by a user of the breast pump device. The primary machine portion is worn on a breast of the user during operation, and the secondary control portion is worn on the neck or head of the user.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated herein and form a part of the specification, illustrate aspects of the present disclosure and, together with the description, further serve to explain the principles of the present disclosure and to enable a person skilled in the pertinent art to make and use the present disclosure.

Figure 1:
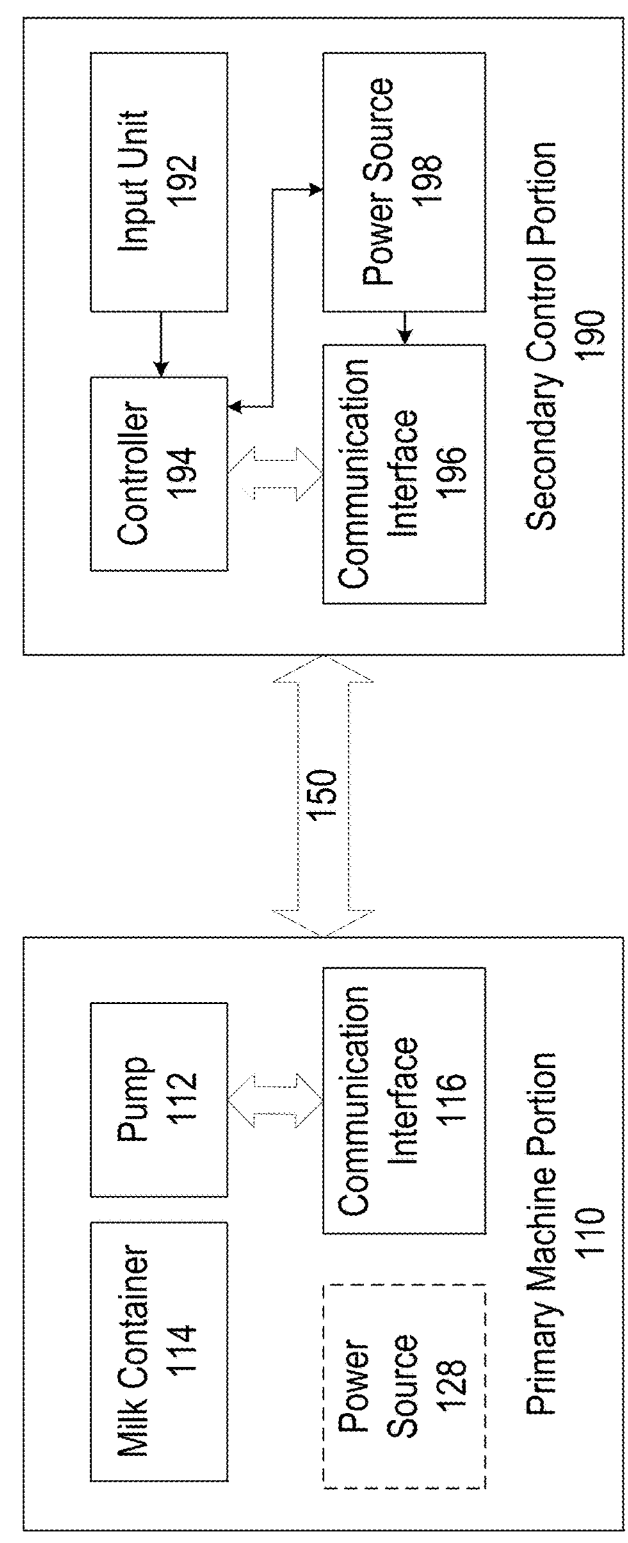
FIG. 1 illustrates a block diagram of an exemplary breast pump device, according to some aspects of the present disclosure.

The present disclosure will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present disclosure. It will be apparent to a person skilled in the pertinent art that the present disclosure can also be employed in a variety of other applications.

It is noted that references in the specification to "one embodiment," "an embodiment," "an example embodiment," "some implementations," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of a person skilled in the pertinent art to affect such feature, structure or characteristic in connection with other implementations whether or not explicitly described.

In general, terminology may be understood at least in part from usage in context. For example, the term "one or more" as used herein, depending at least in part upon context, may be used to describe any feature, structure, or characteristic in a singular sense or may be used to describe combinations of features, structures or characteristics in a plural sense. Similarly, terms such as "a," "an," or "the," again, may be understood to convey a singular usage or to convey a plural usage, depending at least in part upon context. In addition, the term "based on" may be understood as not necessarily intended to convey an exclusive set of factors and may, instead, allow for the existence of additional factors not necessarily expressly described, again, depending at least in part on context.

It should be readily understood that the meaning of "on," "above," and "over" in the present disclosure should be interpreted in the broadest manner such that "on" not only means "directly on" something but also includes the meaning of "on" something with an intermediate feature, a layer, or a structure therebetween, and that "above" or "over" not only means the meaning of "above" or "over" something but can also include the meaning it is "above" or "over" something with no intermediate feature, layer, or structure therebetween (i.e., directly on something).

Further, spatially relative terms, such as "beneath," "below," "lower," "above," "upper," and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The device may be otherwise oriented (e.g., rotated 90 degrees or at other orientations) and the spatially relative descriptors used herein may likewise be interpreted accordingly. In addition, the term "couple," "coupled to," or "coupled between" may be understood as not necessarily intended to be "physically joined or attached," i.e., direct attachment, but can also be interpreted as indirect connection through an intermediate component.

In recent years, working mothers are growing in numbers and have become a significant labor force. However, the society lags behind in providing friendly working conditions and living environments for working mothers, especially those with newborns. On the one hand, doctors and experts are encouraging breastfeeding due to its proven benefits for children. On the other hand, the infrastructure that accommodates breastfeeding is yet to meet the demand of nursing mothers. Lack of access to private spaces when feeding the baby may cause health issues to the nursing mothers, such as awkwardness, congestion of milk within her breast, etc. Innovative gadgets are often used to narrow such a societal gap, an example of which is a breast pump device.

Traditionally, a breast pump device is difficult to shrink in size, because it requires a large air pump to create suction on a breast of a mother. When the pump is integrated into the device, the size of the device only grows larger. Even if it is not integrated, the pump has to connect with other components adjacent to the breast with an airway. This is implemented by, for example, a plastic air line or a vinyl tube. The flexibility of such an airway makes it difficult to store the breast pump device and/or the pump.

To address one or more of the aforementioned issues, the present disclosure introduces a breast pump device, a breast pump system, and a method for operating the same. The breast pump device is easy to be carried around and concealed during use, partly due to its small size and flexible connection between two major functional portions. It also saves nursing mothers from unwanted attention in public when breastfeeding.

FIG. 1 illustrates a block diagram of an exemplary breast pump device 100, according to some aspects of the present disclosure. Breast pump device 100 may include a primary machine portion 110 and a secondary control portion 190. In some embodiments, these two portions are provided as two separate parts of breast pump device 100. For example, primary machine portion 110 may be a self-contained apparatus that does not share any physical components with secondary control portion 190. In another example, when in operation, primary machine portion 110 is adjacent to the user of breast pump device 100 while secondary control portion 190 is at a location relatively away from the user. Thus, primary machine portion 110 and secondary control portion 190 are provided separately according to the present disclosure.

In some embodiments, primary machine portion 110 may include a main housing (not shown in FIG. 1), a pump 112 attached to the main housing, and a milk container 114. It is understood that the components shown in FIG. 1 are exemplary, and other components not listed herein may also be provided in primary machine portion 110. The main housing protects the internal components of primary machine portion 110 from exposure to and damage from the outside environment. The material of the main housing can be plastic, metal, or a combination thereof.

According to the present disclosure, pump 112 may be disposed entirely in the main housing, partially in the main housing, or outside but adjacent to the main housing. In each case, pump 112 is attached to the main housing. In some embodiments, pump 112 may be a mechanical apparatus driven by electrical power that generates a pressure upon a user of breast pump device 100. Pump 112 may be an air pump. When powered on, the air pump may create suction in at least one of its inlet or outlet so that air pressure surrounding the pump may be changed. The changed air pressure is transmitted to the user via, for example, an airway channel (not shown in FIG. 1) and thus exerted upon a breast of the user. Pump 112 according to the present disclosure may include various operation modes. In some embodiments, the suction may be periodically generated, with positive pressure and negative pressure switching between each other at a certain pace. The period is also adjustable based on the user's needs. In some other embodiments, the strength of suction may be controlled by the user to find the most comfortable pressure applied to her breast. These different operation modes may be achieved by adjusting the cycle or power of the electrical components of pump 112. Users can adjust the operation modes by pressing one or more buttons provided on the main housing, or via a remote command from secondary control portion 190, which will be discussed hereinafter.

According to the present disclosure, milk container 114 may be coupled to pump 112 and accommodate breast milk expressed from the user. In some embodiments, milk container 114 is detachably connected to pump 112, and thus may be taken out of the main housing with milk stored therein after pumping operation is complete. For baby's health and safety, milk container 114 may be made of glass, silicone, BPA-free plastic, or a combination of one or more of these materials.

Primary machine portion 110 may further include a communication interface 116, according to some embodiments of the present disclosure. Communication interface 116 may transmit or receive at least one of data or power between itself and other components of breast pumping device 100, including secondary control portion 190. Examples of such components include a processor, a memory, an antenna, a power cable, a power source (such as a power source 128), etc. The transmission may be via wired or wireless settings. In some embodiments, when communication interface 116 receives command data indicative of a user input to secondary control portion 190, it can send control signals to pump 112. As a result, the operation mode of 112 may be changed according to the user input remotely generated on secondary control portion 190, which is located at a different place from primary machine portion 110. In some embodiments, this mode change may be transmitted back to secondary control portion 190, and thus a feedback loop may be established to further optimize the operation of breast pump device 100.

In some embodiments, primary machine portion 110 may further include power source 128. Power source 128 may include a primary battery that is not rechargeable or a secondary battery that is rechargeable. Alternatively, power source 128 may be an AC input from an external power outlet. Power source 128 may provide electrical power to pump 112, communication interface 116, sensor, memory, or any other electrically-powered component inside primary machine portion 110. Power source 128 is not a required component for primary machine portion 110, as the present disclosure allows electrical power to be supplied between primary machine portion 110 and secondary control portion 190 via electrical coupling. Dispensing with power source 128 from primary machine portion 110 may reduce the weight and shrink the size of primary machine portion 110, thus making it easier for the user to conceal it from public view.

In some embodiments, secondary control portion 190 may include a minor housing (not shown in FIG. 1), an input unit 192, a controller 194, a communication interface 196, and a power source 198. It is understood that the components shown in FIG. 1 are exemplary, and other components not listed herein may also be provided in secondary control portion 190. Like the main housing, the minor housing also protects the internal components of secondary control portion 190 from exposure to and damage from the outside environment. The material of the minor housing can be plastic, metal, or a combination thereof.

According to the present disclosure, input unit 192 may be an input apparatus that receives user input, converts the input into one or more of a control signal or data, and transmits the control signal or data to other components inside secondary control portion 190. Examples of input unit 192 include button, keyboard, touchscreen, voice-recognizable microphone, etc. Depending on the type of input unit 192 provided, a user may input her command by finger, palm, voice, etc.

Controller 194 according to the present disclosure may include any appropriate type of general-purpose or special-purpose microprocessor, digital signal processor, or microcontroller. Controller 194 may be configured as a separate processor module dedicated to performing one or more specific functions. Alternatively, controller 194 may be configured as a shared processor module for performing other functions unrelated to the one or more specific functions. Controller 194 may receive a control signal or data from input unit 192, and control the operation of other components inside secondary control portion 190, such as communication interface 196, power source 198, etc. Thus, user control of secondary control portion 190 is implemented.

The user of breast pump device 100 may further control primary machine portion 110 via input to secondary control portion 190. This is made possible via communication interface 196. Similar to communication interface 116, communication interface 196 may transmit or receive at least one of data or power between itself and other components of breast pumping device 100, including primary machine portion 110. Examples of such components include a processor, a memory, an antenna, a power cable, control unit 194, power source 198, etc. The transmission may be via wired or wireless settings.

In some embodiments, when communication interface 196 receives a command data indicative of a user input via input unit 192, it can send control signals to primary machine portion 110 via a communication channel 150. Communication channel 150 may be a wired channel (such as electric wire) or a wireless channel (such as by means of Wi-Fi, Bluetooth, NearLink, or cellular network). This enables the user to control the operation of primary machine portion 110, including pump 112, from the side of secondary control portion 190.

In some embodiments, although not shown in the figures, operation of one or both of primary machine portion 110 or secondary control portion 190 may be performed through applications installed on a smartphone. The smartphone may communicate wirelessly with either or both of primary machine portion 110 or secondary control portion 190 by means of Wi-Fi, Bluetooth, NearLink, or cellular network. The smartphone may send control signals to either or both of the two portions, or receive data (such as status indicator, error message, etc.) therefrom. Once the user navigates through the application, it can direct the operations of one or more components of breast pump device 100, such as cycle, intensity, or peak value of pumping, or on or off of the power source.

In some embodiments, secondary control portion 190 may further include power source 198. Similar to power source 128, power source 198 may also include a primary battery that is not rechargeable or a secondary battery that is rechargeable. Alternatively, power source 198 may be AC input from an external power outlet. Power source 198 may supply power not only to components within secondary control portion 190, but also to primary machine portion 110. The power supply can be achieved via wired or wireless settings. For example, communication channel 150 includes an electric wire, which can transmit power generated by power source 198 to primary machine portion 110, and more specifically, to pump 112. Alternatively, power source 128, if provided in primary machine portion 110, may also supply power to secondary control portion 190 via communication channel 150, and more specifically, to controller 194 and input unit 192. The two-way transmission of power has the benefit of prolonging the use cycle of breast pump device 100.

According to the present disclosure, primary machine portion 110 and secondary control portion 190 are electrically coupled with each other via communication channel 150, which may transmit or receive one or more of an electrical signal or electric power, but not air pressure. This allows a user to remotely operate primary machine portion 110 from the side of secondary control portion 190. Also, because the communication channel 150 is either wireless or in the form of electric wire, it is much more pliant and flexible than traditional air line or tube, making it more convenient for the user to carry and store breast pumping device 100.

In some embodiments, secondary control portion 190 may have a size so small that it can be integrated into other commonly used electronic devices, such as a wearable device. Examples of such devices include headphone, massager, neck-hanging device, ear-hook headset, smartwatch, or smartphone. Using massager as an example, secondary control portion 190 may be formed together with a massager or constructed to perform massaging operations. If it is formed together with a massager, it may communicate with sensors of the massager so that it not only can control the operation of breast pump device 100, but also that of the massager. If it is constructed to perform the massaging operation, it may further include one or more of a sensor, a vibrator, a motor, or a timer that allows it to control the intensity, cycle, or on/off of the massaging operation. Since secondary control portion 190 is integrated into the massager, the user can initiate control of both devices with one set of input units, thus streamlining the hardware configuration of the integrated device. More concrete examples of such applications of secondary control portion 190 will be discussed hereinafter in conjunction with FIGS. 5A to 5E.

Figures 2A, 2B:
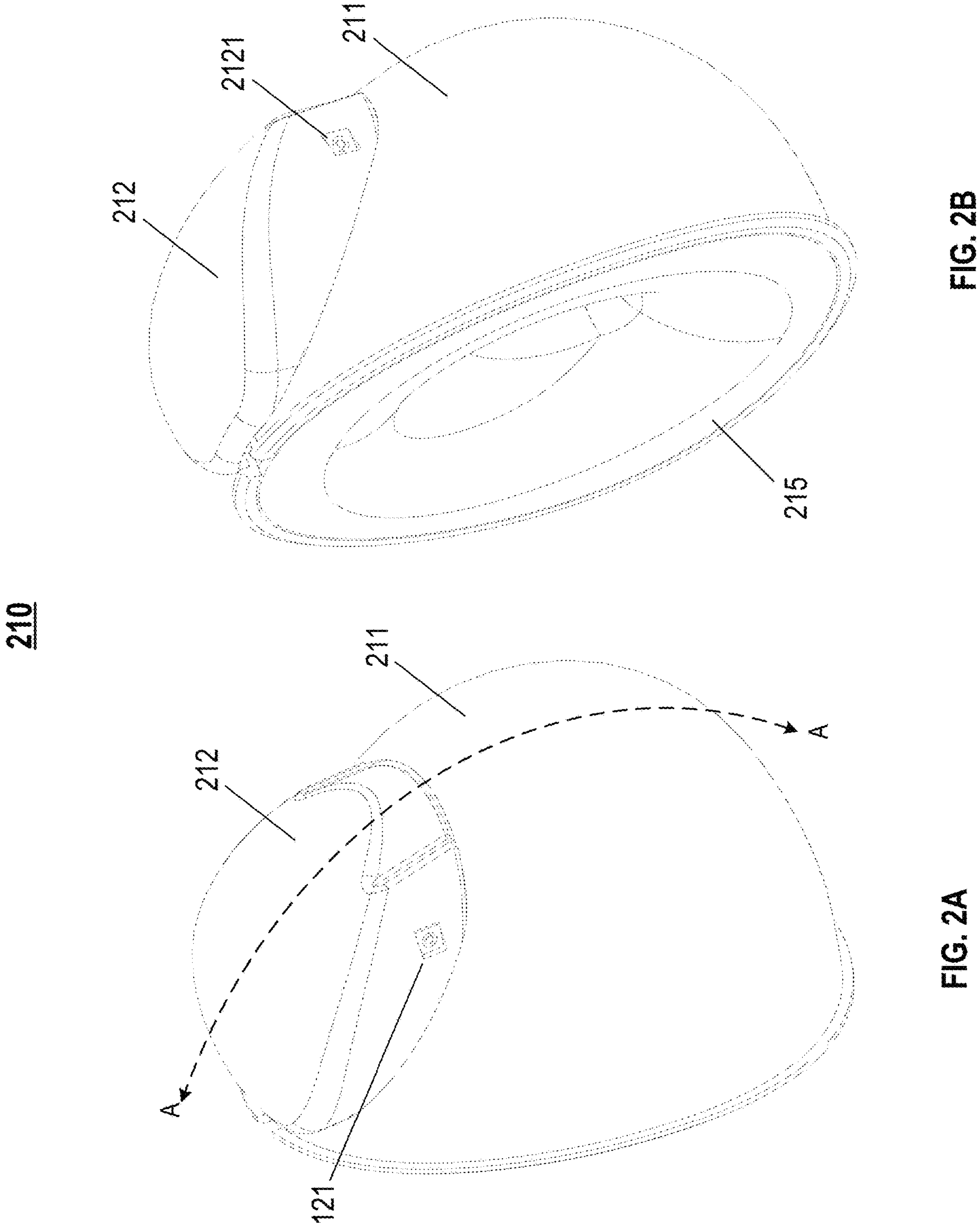
FIG. 2A illustrates a front perspective view of a primary machine portion of an exemplary breast pump device, according to some aspects of the present disclosure.
FIG. 2B illustrates a back perspective view of a primary machine portion of the exemplary breast pump device shown in FIG. 2A, according to some aspects of the present disclosure.

According to some aspects of the present disclosure, FIG. 2A illustrates a front perspective view of a primary machine portion 210 of an exemplary breast pump device; and FIG. 2B illustrates a back perspective view of primary machine portion 210. As shown in FIGS. 2A and 2B, primary machine portion 210 has a main housing 211. Main housing 211 may have a bowl shape that encloses other components of primary machine portion 210. In some embodiments, the main housing may have a different shape or an irregular shape.

According to the present disclosure, primary machine portion 210 also has a pump 212 attached to main housing 211. As shown in FIGS. 2A and 2B, pump 212 is partially disposed in main housing 211, with its upper portion protruding outside main housing 211. An electrical outlet 2121 may be provided on the outer surface of pump 212. The electrical outlet 2121 may be used to connect by wire with another electrical outlet (not shown) of the secondary control portion of the breast pump device. Thus, either or both of data and power may be transmitted between primary machine portion 210 and the secondary control portion. The wire may be detachable from primary machine portion 210. For example, it may have a connector compatible with electrical outlet 2121 and the connector may be plugged into a receptacle of electrical outlet 2121. Alternatively, the wire may be attached to electrical outlet 2121 via magnetic force, in which case a connector may or may not be necessary. In this example, primary machine portion 210 may be charged wirelessly through, e.g., inductive charging. In some other embodiments, the wire may be fixed to primary machine portion 210. In some embodiments, buttons or other input means may also be provided on the outer surface of pump 212 to allow a user to control operations thereof.

In some embodiments, primary machine portion 210 may further include a flange 215 positioned on the backside of primary machine portion 210, as shown in FIG. 2B. Flange 215 may have a round or oval peripheral and a shape similar to a trumpet bell, and may match the opening of main housing 211 in order to form a complete enclosure with main housing 211 to accommodate various components of primary machine portion 210. Flange 215 may connect to an airway channel (e.g., airway channel 213 shown in FIGS. 2C and 2D) and fit with a nipple of a breast of the user.

Figure 2C:
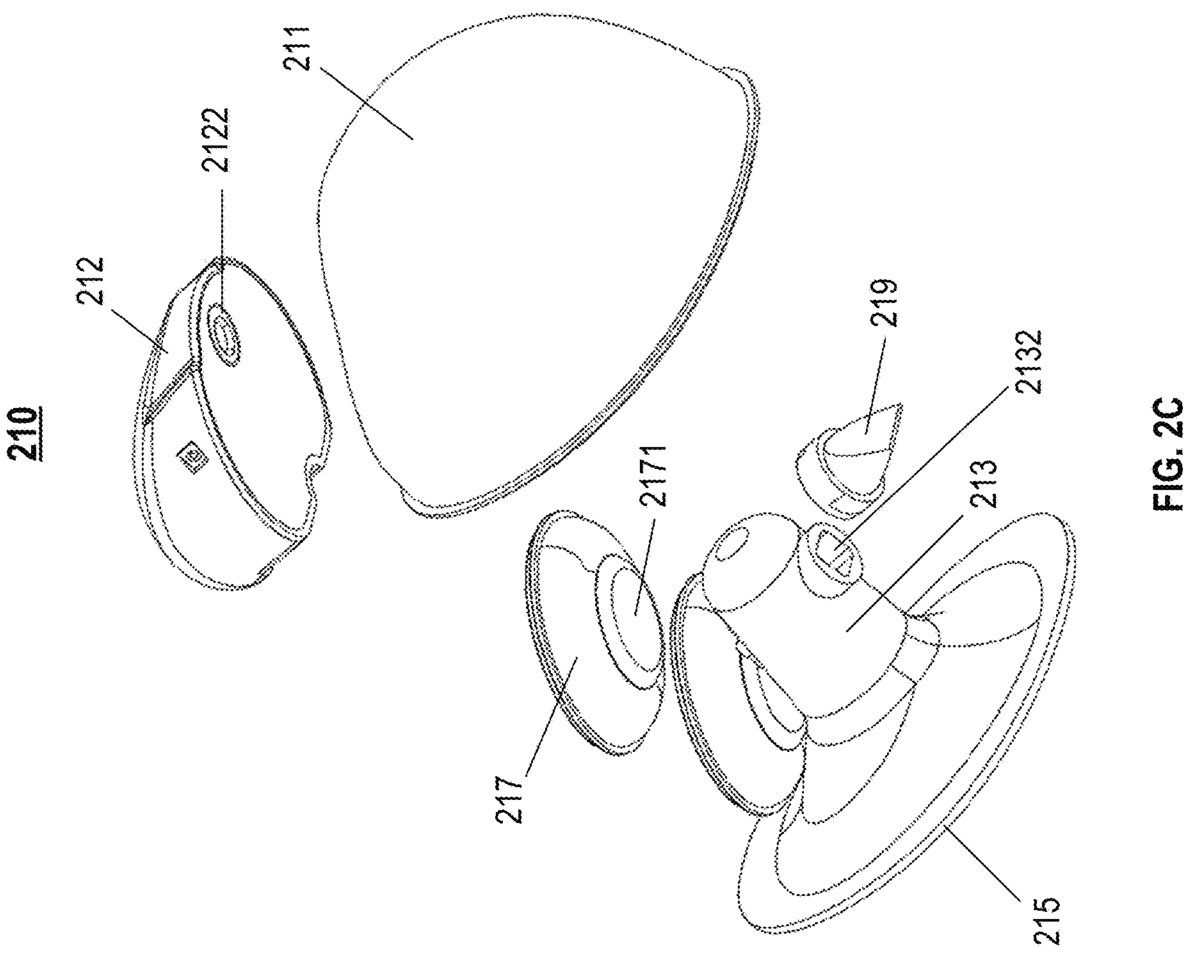
FIG. 2C illustrates an exploded view of the primary machine portion shown in FIG. 2A, according to some aspects of the present disclosure.
Figure 2D:
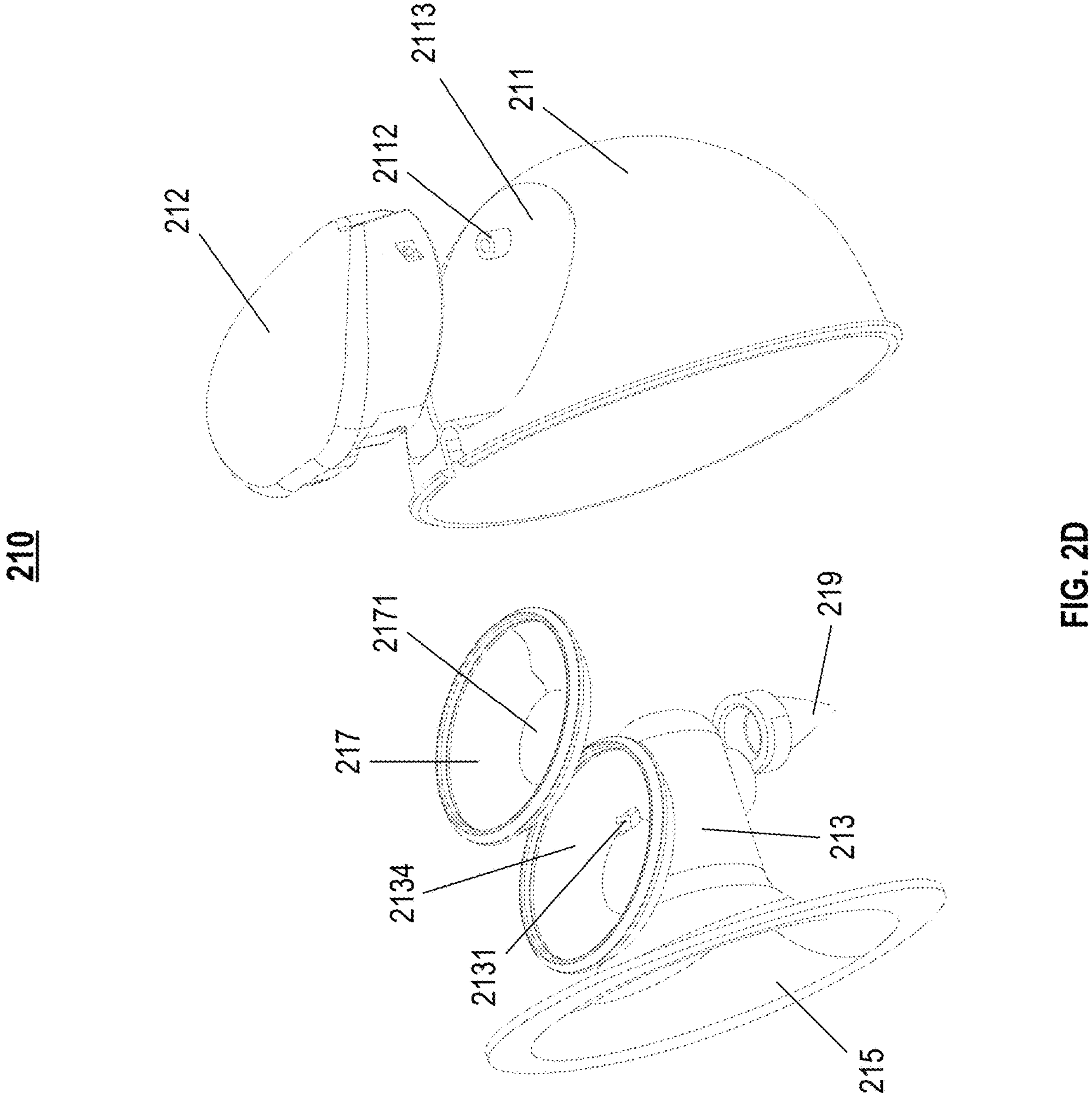
FIG. 2D illustrates another exploded view of the primary machine portion shown in FIG. 2A, according to some aspects of the present disclosure.

FIGS. 2C and 2D illustrate two exploded views of primary machine portion 210 shown in FIG. 2A, according to some aspects of the present disclosure. As shown in FIGS. 2C and 2D, an airway channel 213, a diaphragm unit 217, and a check valve 219 are components of primary machine portion 210 that are accommodated inside the enclosure formed by main housing 211 and flange 215.

Although not shown in FIG. 2C or 2D, primary machine portion 210 may further include a milk container. In some embodiments, the milk container may be formed inside main housing 211 along the inner contour of main housing 211, such as milk container 218 shown in FIG. 2F. This allows the inner space of main housing 211 to be fully utilized, thus minimizing the overall size of primary machine housing 210. In some other embodiments, the milk container may be formed as a separate component (not shown) attached to a side of main housing 211. This makes removal of the milk container convenient because the user does not need to reach inside primary machine housing 210. The milk container may be coupled to pump 212 and accommodate breast milk expressed from the user. There may be other components, such as diaphragm unit 217, check valve 219, and at least a portion of airway channel 213 disposed between the milk container and pump 212. The air pressure generated by pump 212 causes breast milk to flow into the milk container, thus coupling pump 212 with the milk container via an airway.

According to the present disclosure, airway channel 213 may be coupled between pump 212 and the milk container, and does not have to physically contact either pump 212 or the milk container. In some embodiments, airway channel 213 may be a three-way tube, as shown in FIGS. 2C and 2D. The tube has a first opening 2131 facing diaphragm unit 217, a second opening 2132 facing check valve 219, and a third opening (not shown) facing flange 215. In some embodiments, flange 215 may be formed integrally with airway channel 213. Airway channel 213 is hollow inside, thus creating an airway connecting the three openings and the components facing thereto. The airway of airway channel 213 is capable of transmitting negative or positive pressure generated on or near any of the openings to the other remaining openings. In some embodiments, airway channel 213 may include a tee pipe.

As shown in FIGS. 2C and 2D, diaphragm unit 217 is positioned between pump 212 and airway channel 213. Diaphragm unit 217 may fit onto a receiving chamber 2134 attached to first opening 2131 of airway channel 213, thus creating an airtight fitting between diaphragm unit 217 and airway channel 213. Diaphragm unit 217 has a membrane 2171 at its basin. Membrane 2171 is a flexible component that may bend towards a side with relatively small air pressure. Therefore, it may pass a pressure generated by pump 212 to airway channel 213. The pressure may be transmitted to the user's nipple and breast fit within flange 215, thus causing the breast to express milk. In some embodiments, membrane 2171 may oscillate between the side of airway channel 213 and the side of pump 212 when pump 212 creates periodic negative pressure on diaphragm unit 217, thus shifting air pressure inside airway channel 213 to cause the user to continuously express breast milk into the milk container via airway channel 213.

According to the present disclosure, the check valve 219 may function as a one-way exit coupled between airway channel 213 and the milk container, so that the breast milk is allowed to flow from airway channel 213 to the milk container, but is prevented from flowing reversely from the milk container back to airway channel 213. Therefore, the breast milk can be collected inside the milk container without being wasted during use, and the risk of other components of primary machine housing 210 being contaminated by the breast milk is also reduced or eliminated. As shown in FIGS. 2C and 2D, check valve 219 in these embodiments is a duckbill valve. However, the type of check valve is not limited, and may further include one or more of a butterfly check valve, a swing check valve, a diaphragm check valve, or a ball check valve.

Figure 2E:
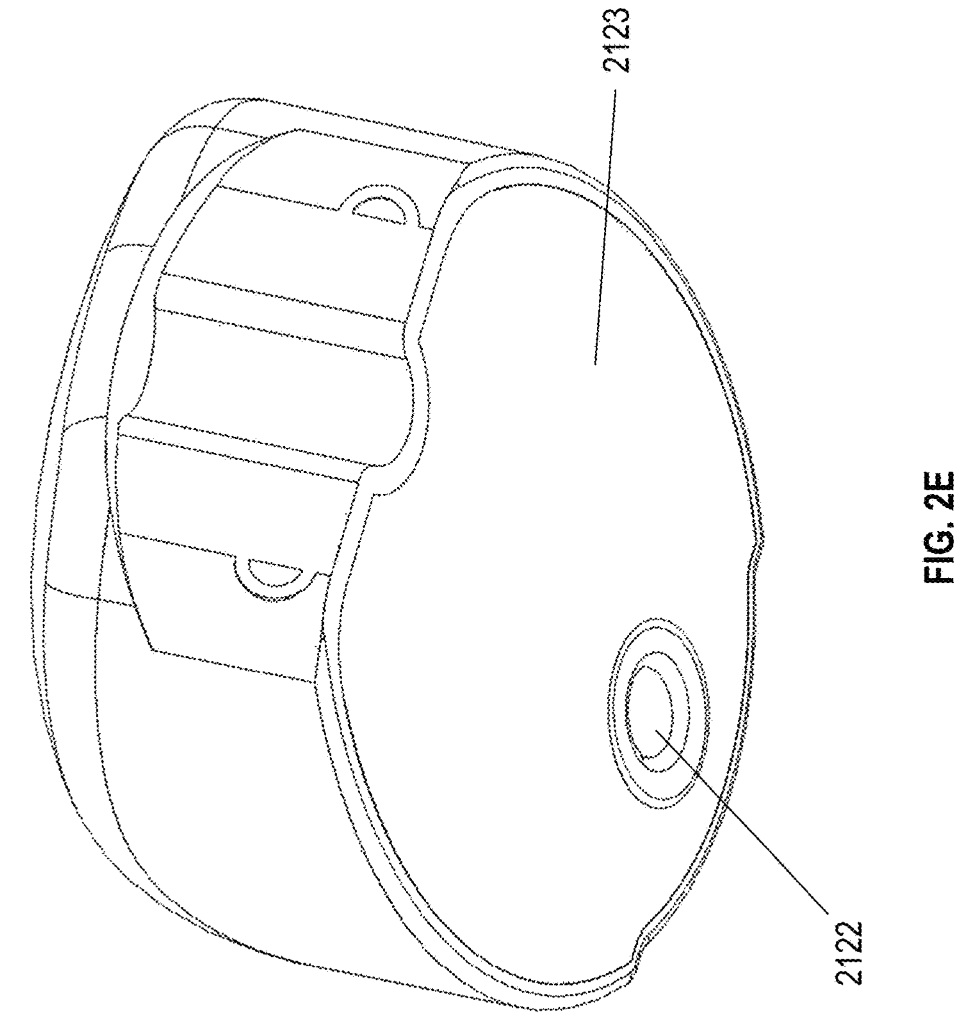
FIG. 2E illustrates a bottom perspective view of a pump of the primary machine portion shown in FIG. 2A, according to some aspects of the present disclosure.

FIG. 2E illustrates a bottom perspective view of pump 212 of primary machine portion 210, according to some aspects of the present disclosure. Pump 212 has a bottom surface 2123, the contour of which matches that of a top surface 2113 of main housing 211 (shown in FIG. 2D). This reduces or eliminates air leakage between pump 212 and main housing 211. Pump 212 further includes a suction hole 2122 on its bottom through which air may be vented in or out of pump 212. Suction hole 2122 is coupled to a suction spout 2112 located on top surface 2113 of main housing 211. During its operation, pump 212 may create negative or positive pressure within main housing 211 through the coupling between suction hole 2122 and suction spout 2112, which is transmitted to diaphragm unit 217, airway channel 213, and the user.

Figure 2F:
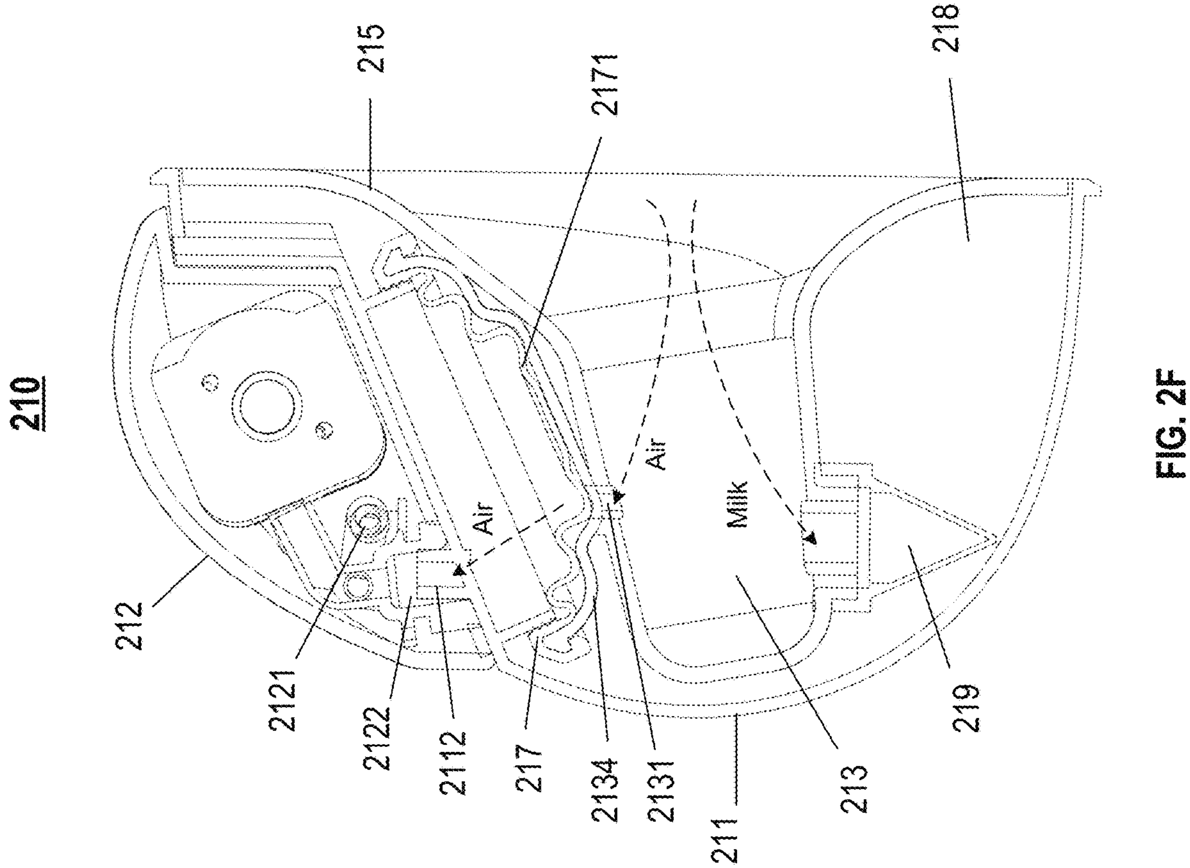
FIG. 2F illustrates a cross-section view of the primary machine portion shown in FIG. 2A along an AA plane, according to some aspects of the present disclosure.

FIG. 2F illustrates a cross-section view of primary machine portion 210 shown in FIG. 2A along an AA plane, according to some aspects of the present disclosure. The numbered components are the same as those with same numbers discussed above in conjunction with FIGS. 2A to 2E, and thus will not be repeated herein. FIG. 2F further illustrates the flow paths of air and milk within airway channel 213 at a moment of operation of primary machine portion 210. In particular, when pump 212 performs suction of air on the upper side of membrane 2171, air on the lower side of membrane 2171 is sucked through first opening 2131 to fill in the space between membrane 2171 and receiving chamber 2134. As a result, membrane 2171 bends upwards, air pressure within airway channel 213 decreases, and the milk is expressed from the user's breast. Although not shown, when pump 212 blows air on the upper side of membrane, the air in the space between membrane 2171 and receiving chamber 2134 is squeezed back into airway channel 213 and thus air pressure within airway channel 123 increases. Therefore, check valve 219 is open and the expressed milk flows into milk container 218.

Figure 3A:
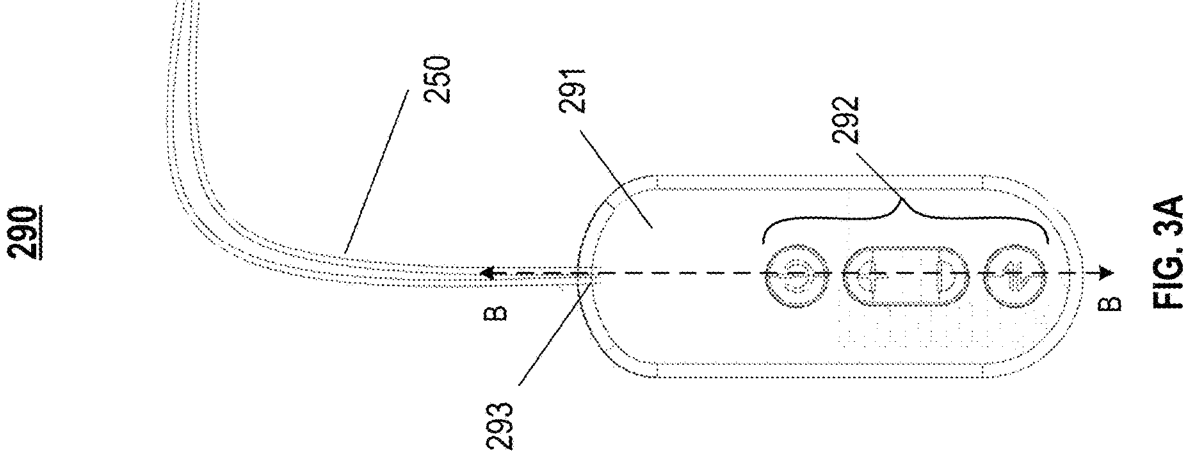
FIG. 3A illustrates a front view of a secondary control portion of an exemplary breast pump device, according to some aspects of the present disclosure.

FIG. 3A illustrates a front view of a secondary control portion 290 of an exemplary breast pump device, according to some aspects of the present disclosure. Secondary control portion 290 may have a minor housing 291 protecting internal components from exposure to and damage from the outside environment. Minor housing 291 may include an upper part and a lower part being attached or sealed together.

Secondary control portion 290 may also include an input unit. In some embodiments, the input unit may be provided at the front of minor housing 291 with one or more input buttons 292, as shown in FIG. 3A. Input buttons 292 may be touched by a user of the breast pumping device to control the operation of primary machine portion 210. For example, one button may be a power button that turns on or off primary machine portion 210. A pair of buttons may increase or decrease the pumping intensity of pump 212. Another button may switch among different operation modes of pump 212. Examples of the input unit are not limited herein.

In some embodiments, secondary control portion 290 may be electrically coupled to primary machine portion 210 by a wire 250, as shown in FIG. 3A. Wire 250 may transmit power, data, or both between primary portion 210 and secondary control portion 290. Wire 250 may be connected to secondary control portion 290 via an electrical outlet 293, which is provided on the outer surface of secondary control portion 290. In some embodiments, wire 250 may be detachable from secondary control portion 290. It can be plugged into a receptacle of electrical outlet 293. Alternatively, wire 250 may be attached to electrical outlet 293 via magnetic force, in which case a connector may or may not be necessary. In this example, secondary control portion 290 may be charged wirelessly through, e.g., inductive charging. In some other embodiments, wire 250 may be fixed to secondary control portion 290.

Although not shown, it is understood that secondary control portion 290 may be wirelessly coupled to primary machine portion 210, as discussed in conjunction with FIG. 1. Wireless connection may be achieved by means of Wi-Fi, Bluetooth, NearLink, or cellular network.

Figure 3B:
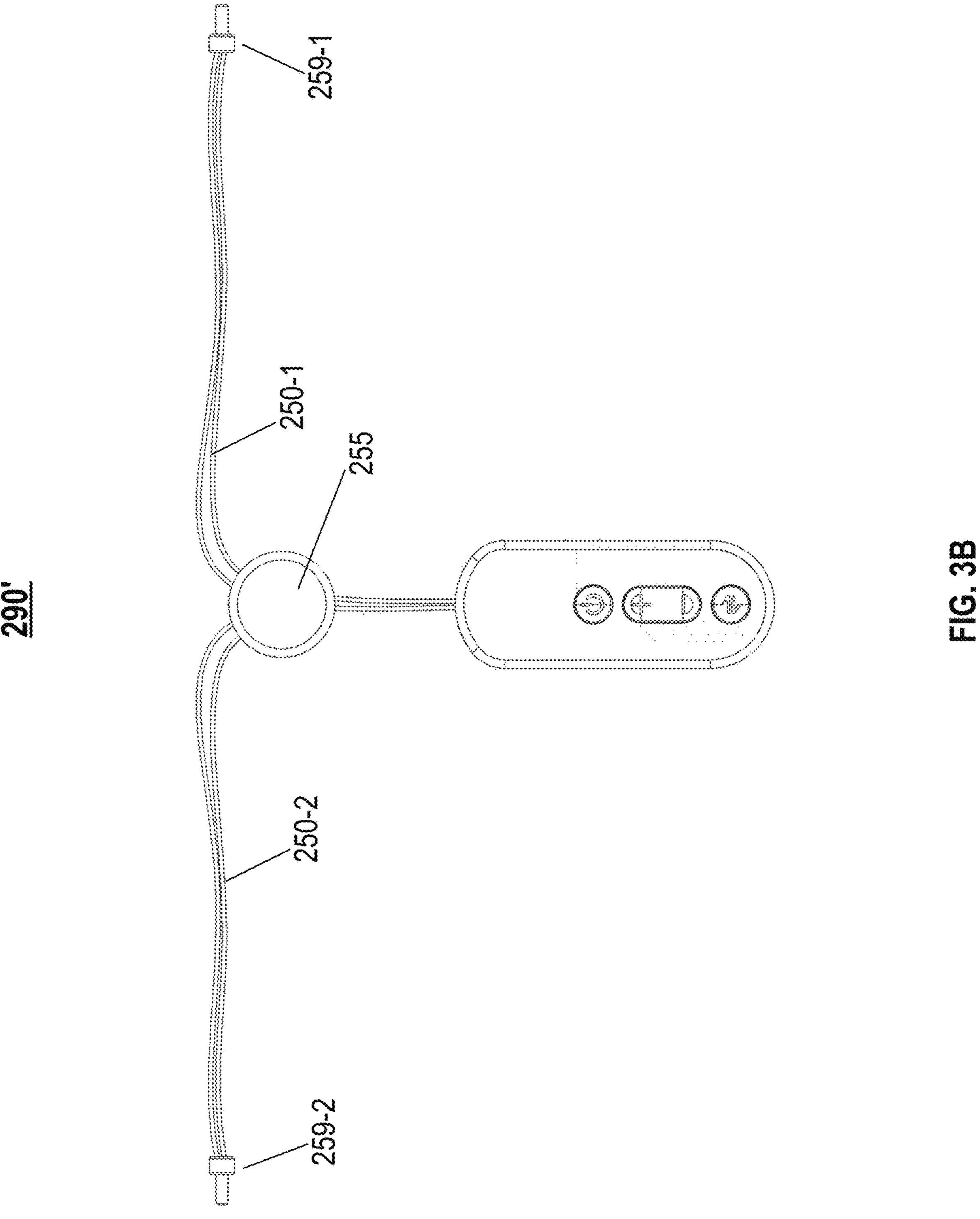
FIG. 3B illustrates a front view of another secondary control portion of an exemplary breast pump device, according to some aspects of the present disclosure.

FIG. 3B illustrates a front view of another secondary control portion 290', according to some aspects of the present disclosure. Secondary control portion 290' differs from secondary control portion 290 shown in FIG. 3A in that it has two wires 250-1, 250-2 leading to two different primary machine portions. Accordingly, each wire has a connector 259-1 or 259-2 to be coupled to its respective primary machine portion. Secondary control portion 290' further includes a retractable reel 255 that allows the user to easily extend or retract the wires 250-1, 250-2, so that the lengths thereof can be adjusted.

Figure 3C:
FIG. 3C illustrates a cross-section view of the secondary control portion shown in FIG. 3A along a BB plane, according to some aspects of the present disclosure.
Figure 3C:
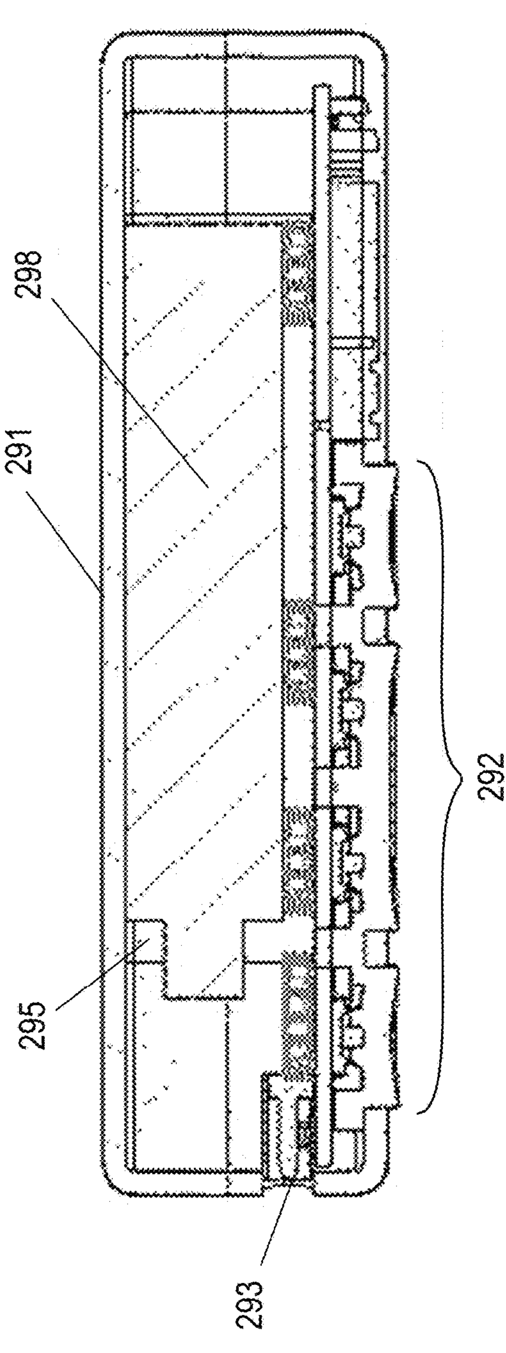

FIG. 3C illustrates a cross-section view of secondary control portion 290 shown in FIG. 3A along a BB plane, according to some aspects of the present disclosure. The numbered components are the same as those with the same numbers discussed above in conjunction with FIGS. 3A and 3B, and thus will not be repeated herein.

Secondary control portion 290 may further include a power source 298, as shown in FIG. 3C. As discussed in conjunction with FIG. 1, power source 298 may include a primary battery or a secondary battery. Power source 298 may be disposed inside minor housing 291, with its length extending along with that of secondary control portion 290. According to the present disclosure, power source 298 may not only supply electric power to components of secondary control portion 290, it may also provide electric power to primary machine portion 210 via wired or wireless settings.

A circuit board 295 may also be provided within secondary control portion 290. In some embodiments, circuit board 295 includes at least one processor and at least one memory, among other components. The at least one processor may be any appropriate type of general-purpose or special-purpose microprocessor, digital signal processor, or microcontroller, and performs one or more specific functions associated with a controller (e.g., controller 194 discussed in conjunction with FIG. 1). The at least one memory may store the computer programs to be executed by the at least one processor, or the output of the at least one processor which may be used for control of secondary control portion 290 or primary machine portion 210. In some embodiments, circuit board 295 includes at least one antenna. The at least one antenna may function as a communication interface (e.g., communication interface 116 discussed in conjunction with FIG. 1) that transmits or receives data between secondary control portion 290 and primary machine portion 210. In some embodiments, circuit board 295 includes at least one power connector, which may also be part of the communication interface and transmit electric power between secondary control portion 290 and primary machine portion 210.

Figure 4:
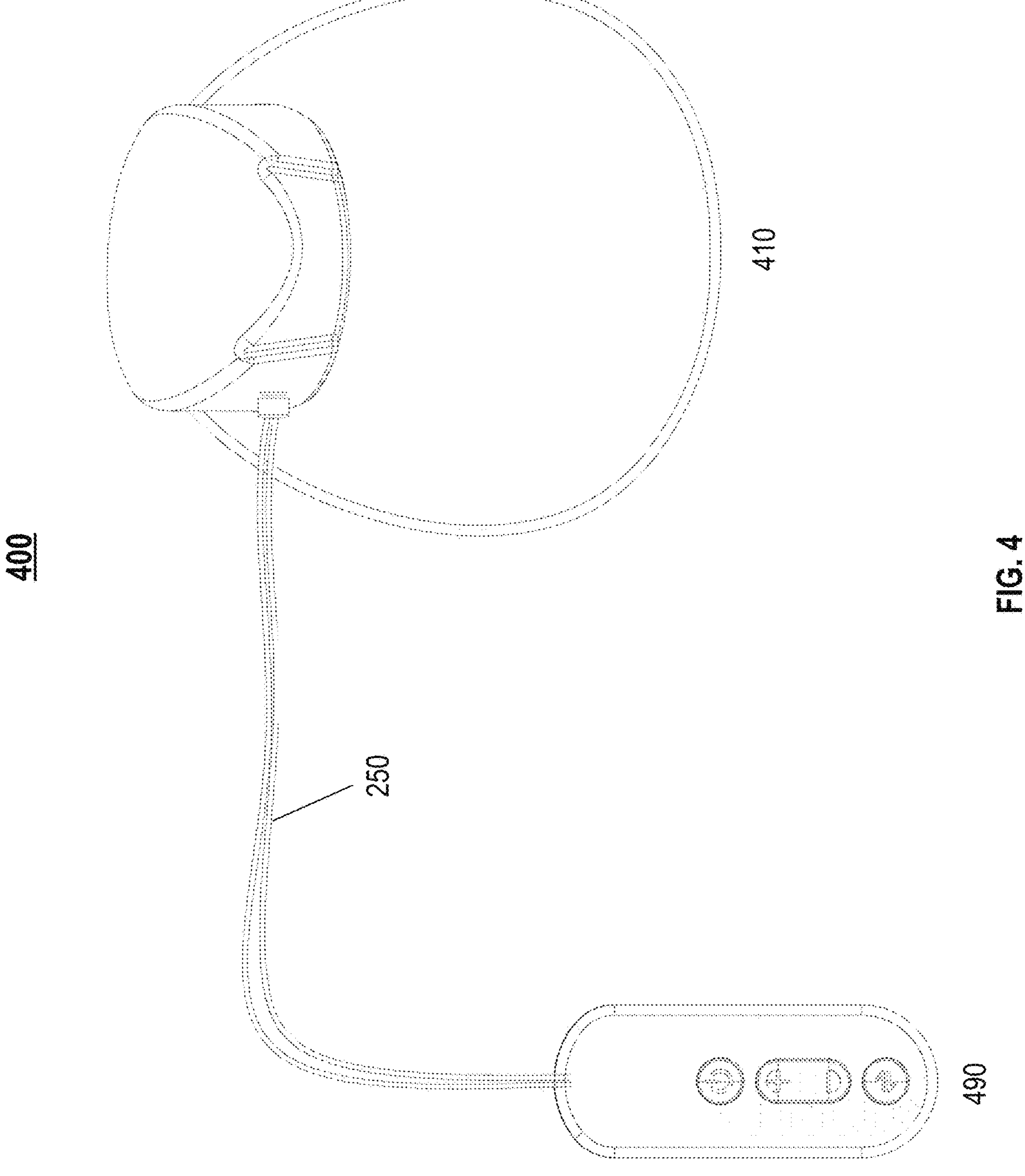
FIG. 4 illustrates a front perspective view of an exemplary breast pump device with one primary machine portion and one secondary control portion, according to some aspects of the present disclosure.

FIG. 4 illustrates a front perspective view of an exemplary breast pump device 400 with one primary machine portion 410 and one secondary control portion 490, according to some aspects of the present disclosure. Primary machine portion 410 may be any of the primary machine portions described herein, including primary machine portions 110 and 210 described above. Secondary control portion 490 may be any of the secondary control portions described herein, including secondary control portions 190 and 290 described above.

As shown in FIG. 4, primary machine portion 410 is coupled to secondary control portion 490 via a wire 450. Wire 450 may include one or more electric wires. In some embodiments, wire 450 may be detachable from at least one of primary machine portion 410 and secondary control portion 490. According to the present disclosure, wire 450 does not provide any airway between the two portions, and thus can be designed to be much smaller in diameter and lighter in weight than air line or tube. Moreover, electric wires are much more flexible, and thus easier to be bent and stored than air line or tube. Electric wires are also capable of transmitting data, power, or both, none of which is possible with air line or tube. The length of electric wires can be adjusted by a retractable reel (e.g., retractable reel 255 in FIG. 3B), which is inapplicable to air line or tube due to obstruction of its airway. Although not shown in FIG. 4, it is understood that primary machine portion 410 may be wirelessly coupled to secondary control portion 490 by means of Wi-Fi, Bluetooth, NearLink, or cellular network.

Figure 5A:
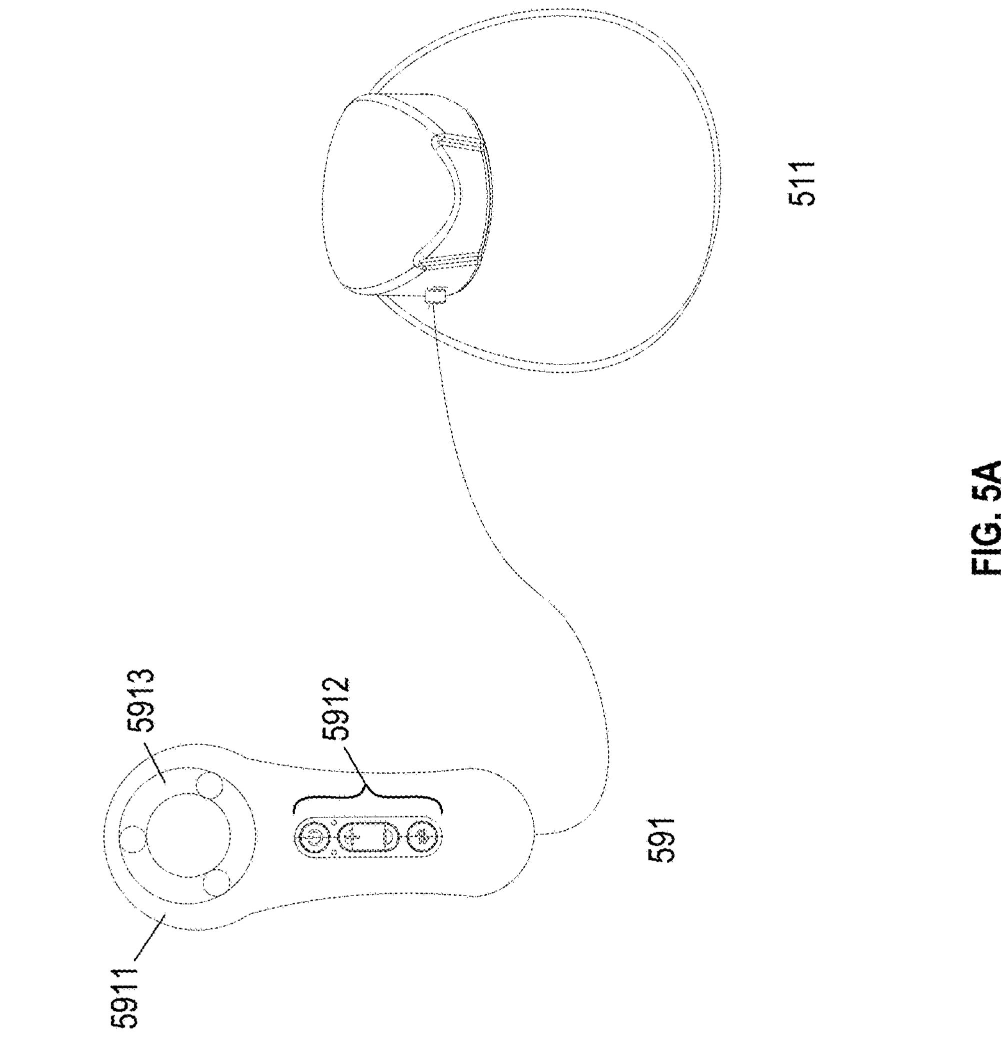
FIG. 5A illustrates an application of a secondary control portion to a massager, according to some aspects of the present disclosure.

FIG. 5A illustrates an application of a secondary control portion 591 to a massager, according to some aspects of the present disclosure. In this example, secondary control portion 591 is constructed to perform massaging operations. The lower portion of secondary control portion 591 has a similar configuration as secondary control portion 290 described above in conjunction with FIGS. 3A to 3C, for example, including input buttons 5912. Different from secondary control portion 290, the upper portion of secondary control portion 591 is provided with a massager 5911 having one or more kneading protrusions 5913. In some embodiments, a battery may be enclosed within massager 5911 to power the operations of at least one of massager 5911, secondary control portion 591, or primary machine portion 511.

In some embodiments, the operations of massager 5911 may be controlled by user input through input buttons 5912. For example, a user may press the mode-switch button of input buttons 5912, which may switch control between primary machine portion 511 and massager 5911. After the mode is switched to massaging operations, the user can further control the massaging intensity, cycle, duration, mode, etc. by pressing the increase or decrease buttons. During massaging operations, the kneading protrusions 5913 may each move independently or collectively (e.g., circling around the massager). Compared to a standalone secondary control portion (e.g., secondary control portion 290), secondary control portion 591 may further include one or more of a sensor, a vibrator, a motor, or a timer.

Figure 5B:
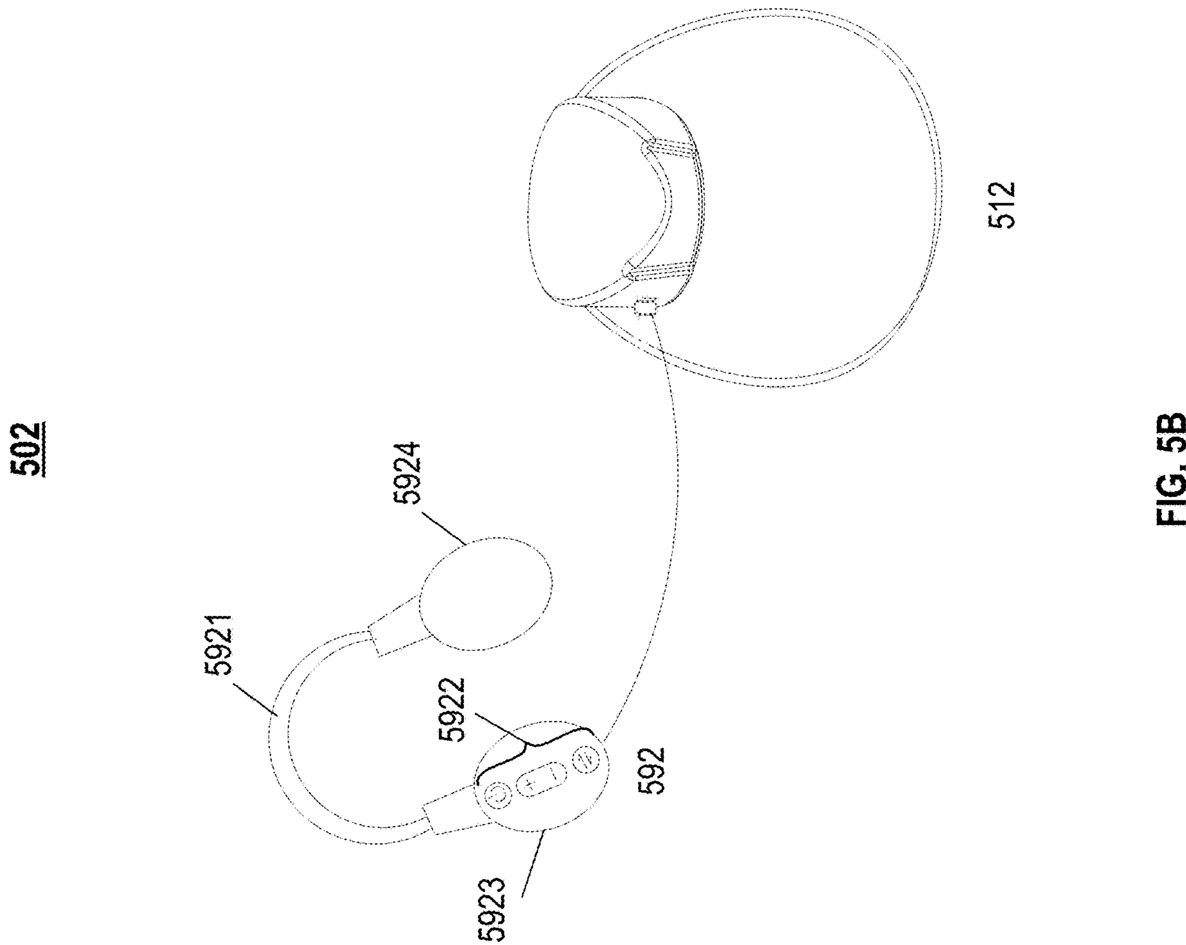
FIG. 5B illustrates an application of a secondary control portion to a headphone, according to some aspects of the present disclosure.

FIG. 5B illustrates an application of a secondary control portion 592 to a headphone, according to some aspects of the present disclosure. The headphone may include two earpieces 5923, 5924 and a headband 5921 connecting the two earpieces. In this example, secondary control portion 592 is integrated into at least one earpiece of the headphone, for example, earpiece 5923. Earpiece 5923 has similar configuration as secondary control portion 290 described above in conjunction with FIGS. 3A to 3C, for example, including input buttons 5922 provided on the outer surface thereof. In addition, earpiece 5923 may also include a speaker, a battery, and a microphone. The battery may function as a power source similar to power source 198 or 298 described above. The microphone may be equipped with voice recognition capability, so that a user may control the operations of primary machine portion 512, secondary control portion 592, the headphone, or any combination of the above via his or her voice. In some embodiments, the operations can be divided between two earpieces 5923, 5924, each having input units, so that one earpiece may control operations of primary machine portion 512 while the other may control operations of secondary control portion 592 or the headphone.

Figure 5C:
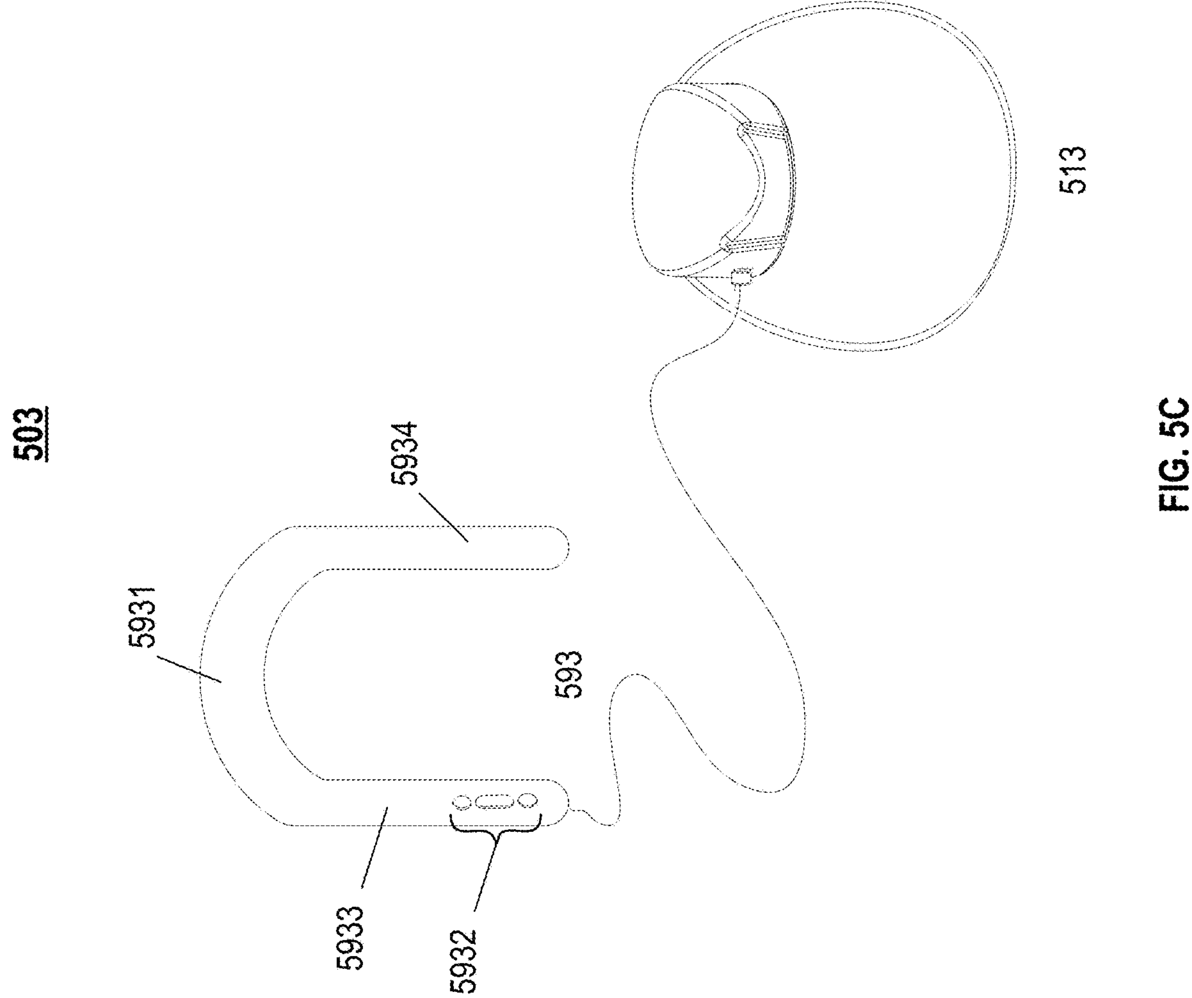
FIG. 5C illustrates an application of a secondary control portion to a neck-hanging device, according to some aspects of the present disclosure.

FIG. 5C illustrates an application of a secondary control portion 593 to a neck-hanging device, according to some aspects of the present disclosure. The neck-hanging device may include two arms 5933, 5934 and one neckband 5931 connecting the two arms. In this example, secondary control portion 593 is integrated into at least one arm of the neck-hanging device, for example, arm 5933. Arm 5923 has similar configuration as secondary control portion 290 described above in conjunction with FIGS. 3A to 3C, for example, including input buttons 5932 provided on the outer surface thereof. In addition, arm 5933 may also include at least one of a speaker, a fan, or a motor. It may also include a battery, which may function as a power source similar to power source 198 or 298 described above. In some embodiments, the operations can be divided between two arms 5933, 5934, each having input units, so that one arm may control operations of primary machine portion 513 while the other may control operations of secondary control portion 593 or the neck-hanging device.

Figure 5D:
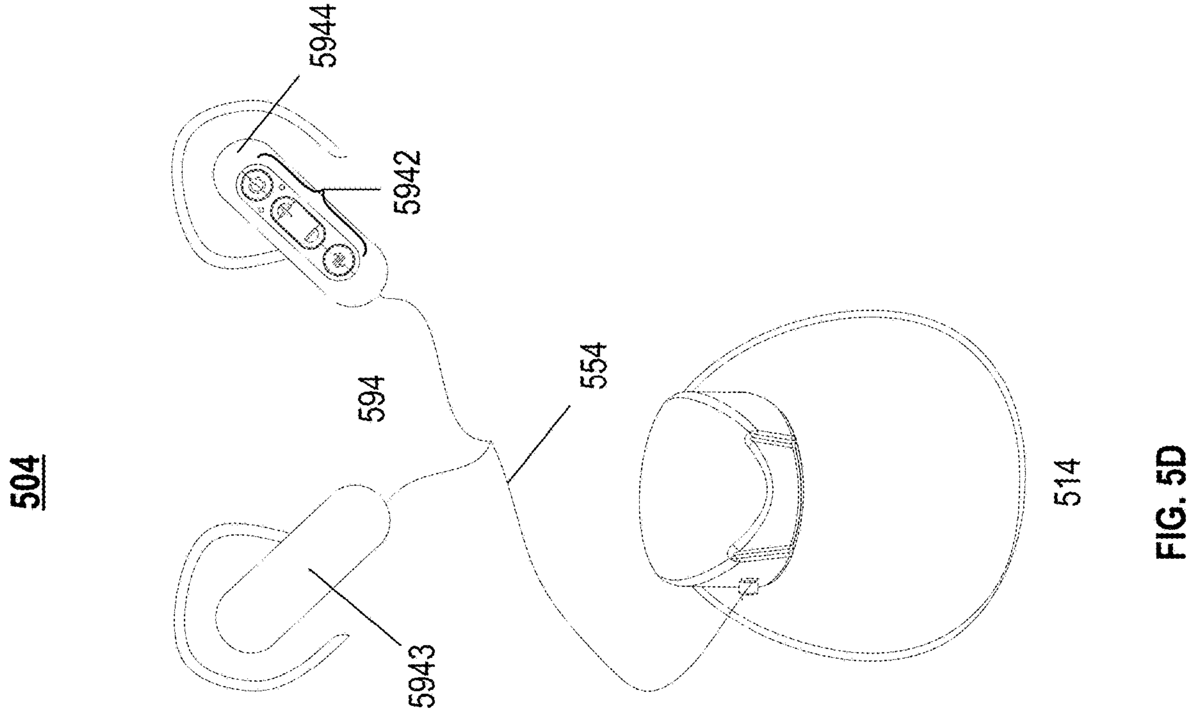
FIG. 5D illustrates an application of a secondary control portion to an ear-hook headset, according to some aspects of the present disclosure.

FIG. 5D illustrates an application of a secondary control portion 594 to an ear-hook headset, according to some aspects of the present disclosure. The ear-hook headset may include two earpieces 5943, 5944. In this example, secondary control portion 594 is integrated into at least one earpiece of the neck-hanging device, for example, earpiece 5944. Earpiece 5944 has similar configuration as secondary control portion 290 described above in conjunction with FIGS. 3A to 3C, for example, including input buttons 5942 provided on the outer surface thereof. In addition, earpiece 5944 may also include at least one of a speaker, a battery, and a microphone. The battery may function as a power source similar to power source 198 or 298 described above. The microphone may be equipped with voice recognition capability, so that a user may control the operations of primary machine portion 514, secondary control portion 594, the headphone, or any combination of the above via his or her voice. In some embodiments, the operations can be divided between two earpieces 5943, 5944, both having input units, so that one earpiece may control operations of primary machine portion 514 while the other may control operations of secondary control portion 594 or the ear-hook headset. As shown in FIG. 5D, two earpieces 5943, 5944 may be connected by a wire 554, which has a third end coupling primary machine portion 514 with the two earpieces as well as secondary control portion 594.

Figure 5E:
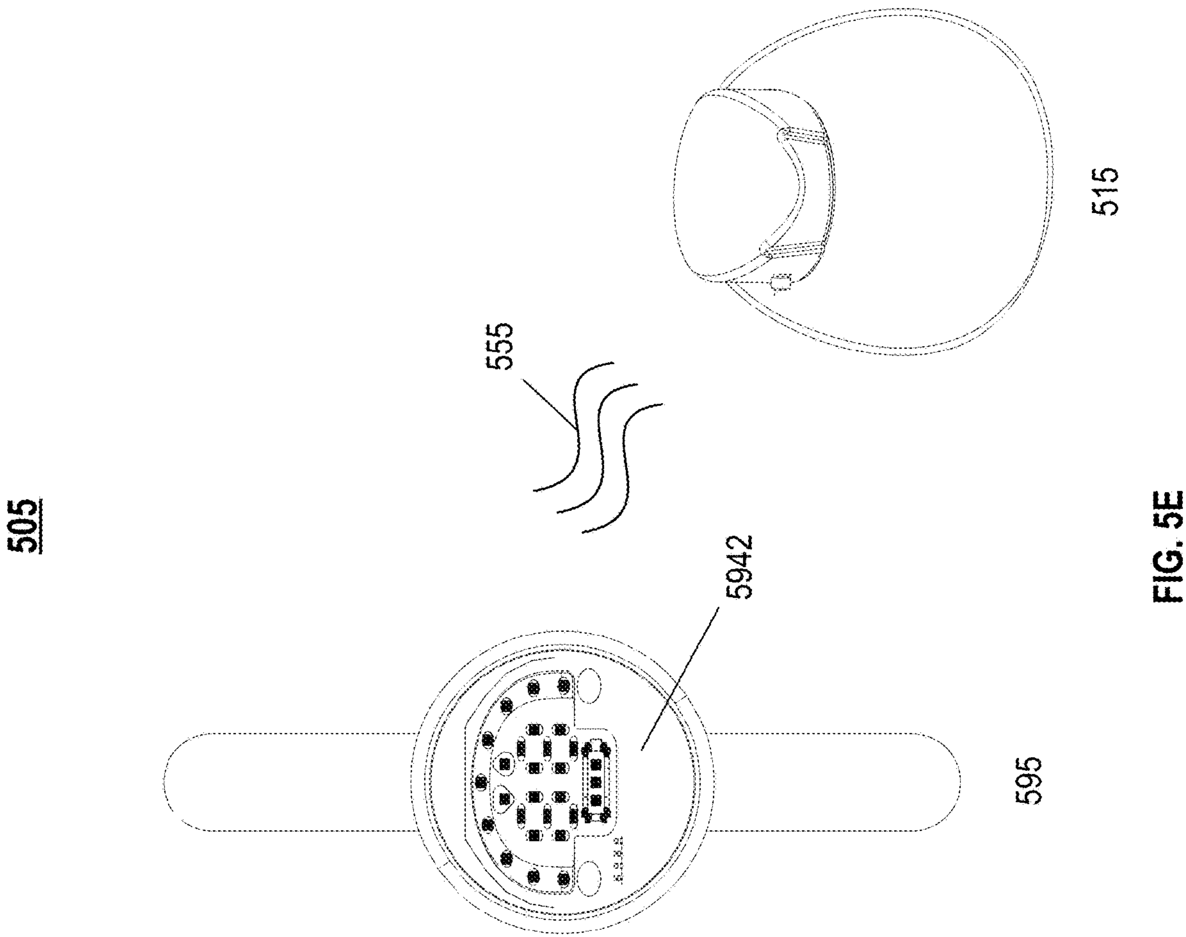
FIG. 5E illustrates an application of a secondary control portion to a smartwatch, according to some aspects of the present disclosure.

FIG. 5E illustrates an application of a secondary control portion 595 to a smartwatch, according to some aspects of the present disclosure. In this example, secondary control portion 595 is integrated into the smartwatch. The smartwatch may include a touchscreen, a battery, and a microphone. The touchscreen may replace input buttons and serve as an interface for the user of the breast pumping device to input its desired operations to one or more of primary machine portion 515, secondary control portion 595, or the smartwatch. The smartwatch-integrated secondary control portion 595 may be coupled to primary machine portion 515 via a wireless channel 555. Alternatively, secondary control portion 595 and primary machine portion 515 may be coupled by attaching to each other via magnetic force. Either secondary control portion 595 or primary machine portion 515 can be charged by the other via wireless charging. The battery may function as a power source similar to power source 198 or 298 described above. The microphone may be equipped with voice recognition capability, so that a user may control the operations of primary machine portion 515, secondary control portion 595, the smartwatch, or any combination of the above via his or her voice.

In some embodiments, the secondary control portion may be integrated into a smartphone. Similar to the smartwatch, the smartphone may also include a touchscreen, a battery, and a microphone. The touchscreen may replace input buttons and serve as an interface for the user of the breast pumping device to input its desired operations on one or more of the primary machine portion, the secondary control portion, and the smartphone. The smartphone-integrated secondary control portion may be coupled to the primary machine portion via a wireless channel. Alternatively, the secondary control portion and the primary machine portion may be coupled by attaching to each other via magnetic force. Either the secondary control portion or the primary machine portion can be charged by the other via wireless charging. The battery may function as a power source similar to power source 198 or 298 described above. The microphone may be equipped with voice recognition capability, so that a user may control the operations of the primary machine portion, the secondary control portion, the smartphone, or any combination of the above via his or her voice. The smartphone may be installed with software applications to achieve the controlling operations described herein.

Figure 6A:
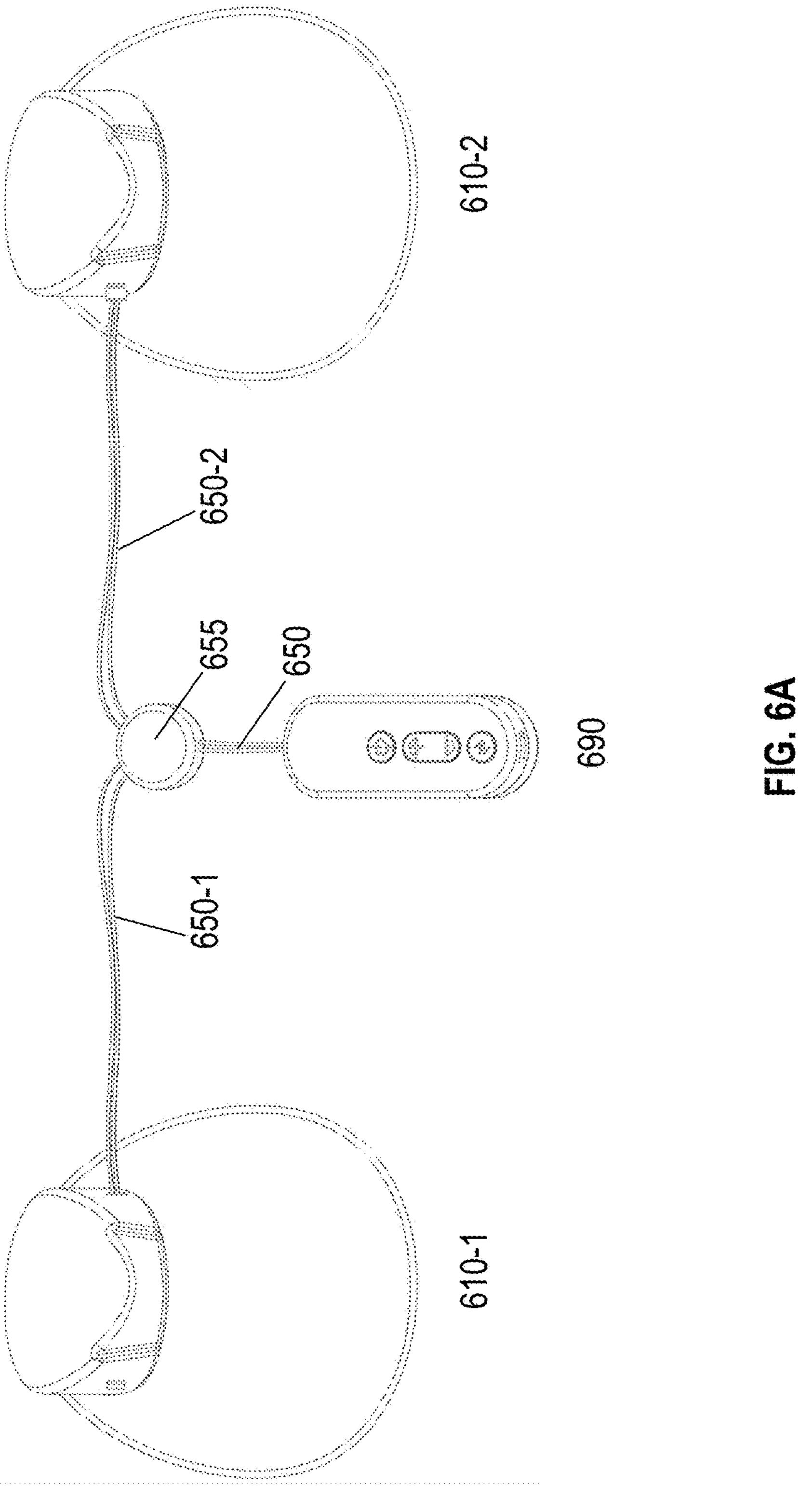
FIG. 6A illustrates a front perspective view of an exemplary breast pump system with two primary machine portions and one secondary control portion, according to some aspects of the present disclosure.

FIG. 6A illustrates a front perspective view of an exemplary breast pump system 600 with two primary machine portions 610-1, 610-2 and one secondary control portion 690, according to some aspects of the present disclosure. Breast pump system 600 may be worn by a user on both breasts, thus allowing simultaneous expressing of milk while also being capable of adjusting pumping parameters collectively for both sides or independently for each side. Each of primary machine portions 610-1 and 610-2 has the same or similar configurations as other primary machine portions described herein, such as primary machine portion 110, 210, 410, 511, 512, 513, 514, or 515. Secondary control portion 690 also has the same or similar configurations as other secondary control portions described herein, such as secondary control portion 190, 290, 490, 591, 592, 593, 594, or 595. Thus, their detailed descriptions will not be repeated herein.

As shown in FIG. 6A, each of the primary machine portions 610-1 and 610-2 is coupled to the same secondary control portion 690. The coupling is achieved through a three-way wire 650. A retractable reel 655 divides wire 650 into two branches 650-1, 650-2, with one branch connecting to one primary machine portion respectively. Therefore, two wire routes are established, one coupling primary machine portion 610-1 to secondary control portion 690 and the other coupling primary machine portion 610-2 to secondary control portion 690. This wire configuration is the same as that described in conjunction with FIG. 3B. In some embodiments, secondary control portion 690 may further include a switching unit (not shown) that switches transmission of data, power, or both between the two wire routes. The switching unit may be implemented by hardware, such as a switching button and a circuit converting analog input signals into digital control signals, or by software, such as computer-readable programs or codes that can be loaded and executed by at least one processor within the system. The switching unit can be triggered by a user input (e.g., through a switching button) or the system automatically (e.g., through programs executable upon meeting certain predetermined conditions). Thus, each wire route can be distinct from the other, allowing operations of the two primary machine portions 610-1, 610-2 to be performed independently from each other. For example, when primary machine portion 610-1 operates at a speed of one pumping per second, primary machine portion 610-2 operates at a speed of two pumping per second. It is also possible to align the operations of two primary machine portions 610-1, 610-2 to be the same, which may eliminate discrepancies between the two sides of milk expressing.

In some embodiments, the two primary machine portions 610-1, 610-2 are capable of communicating with each other. This is implemented by transmitting data directly between themselves or through an intermediate component (e.g., secondary control portion 690). As shown in FIG. 6A, data may be transmitted from primary machine portion 610-1 to primary machine portion 610-2 via wire 650-1, wire 650, and wire 650-2, with or without passing through secondary control portion 690. The data may indicate one or more parameters of the operation of the primary machine portion, such as the operation status. The operation status may include one or more of in-operation, hibernation, power-off, operation mode, operation intensity, or circulation period. The user can set a maximum discrepancy threshold between the two primary machine portions 610-1, 610-2, so that exceeding the threshold would cause both primary machine portions 610-1, 610-2 to stop working. In order to avoid such undesirable scenarios, one or both of primary machine portions 610-1, 610-2 may adjust their respective operation status based on the data communicated from and indicative of the operation status of the other primary machine housing.

Figure 6B:
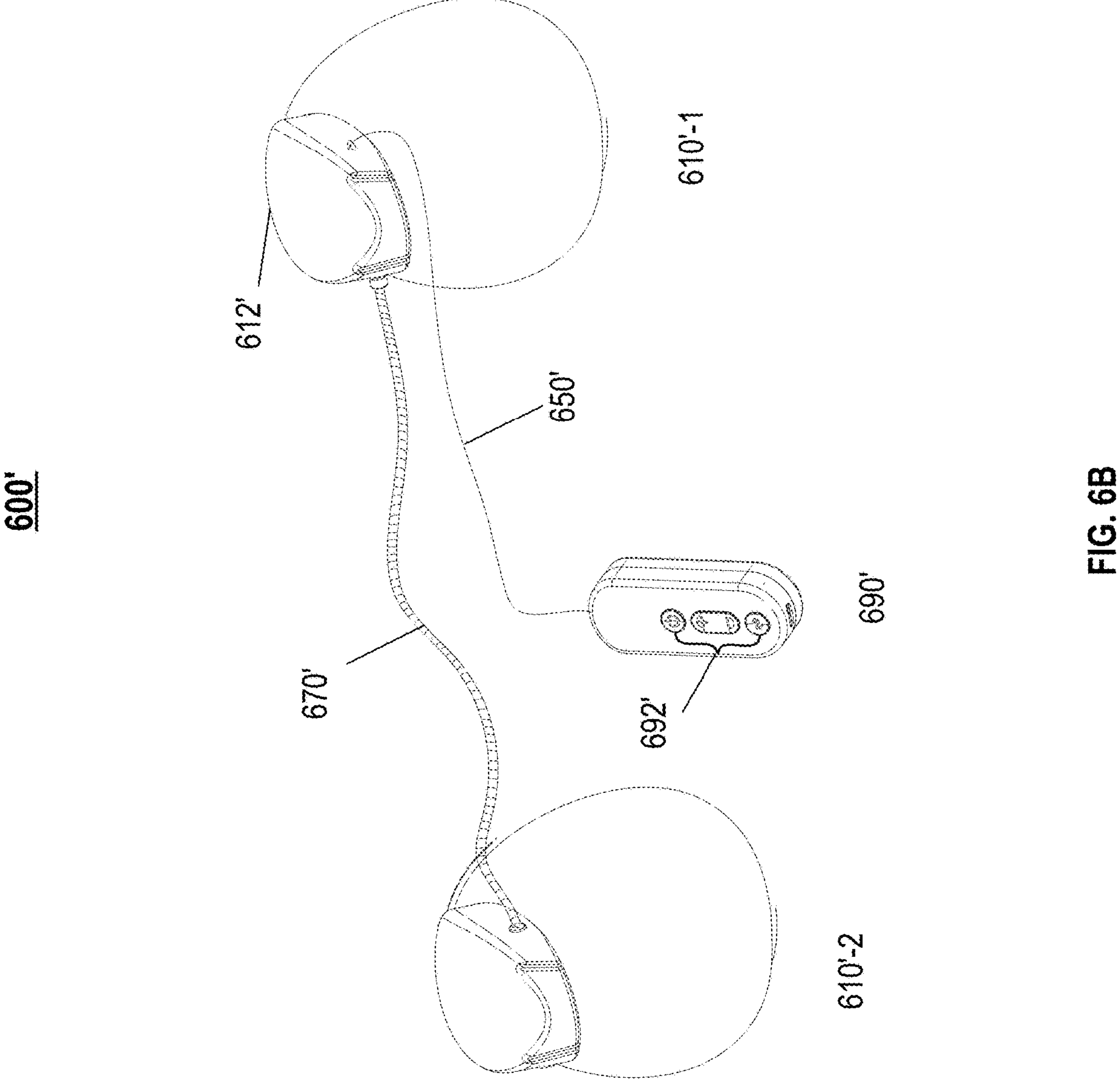
FIG. 6B illustrates a front perspective view of another exemplary breast pump system with two primary machine portions and one secondary control portion, according to some aspects of the present disclosure.

FIG. 6B illustrates a front perspective view of another exemplary breast pump system 600' with two primary machine portions 610'-1, 610'-2 and one secondary control portion 690', according to some aspects of the present disclosure. In this example, secondary control portion 690' is only electrically coupled to one of the two primary machine portions, that is, primary machine portion 610'-1, and the two primary machine portions 610'-1 and 610'-2 are connected by an airway 670'. Primary machine portion 610'-1 has a pump 612', as shown in FIG. 6B. Primary machine portion 610'-2 may or may not have a pump. When primary machine portion 610'-2 has a pump, it functions in a same or similar way as either one of the two primary machine portions described in conjunction with FIG. 6A. When primary machine portion 610'-2 does not have a pump, the pumping operations thereof may be provided by pump 612' of first primary machine portion, which in turn may be controlled by a user input via input units 692'.

Figure 7A:
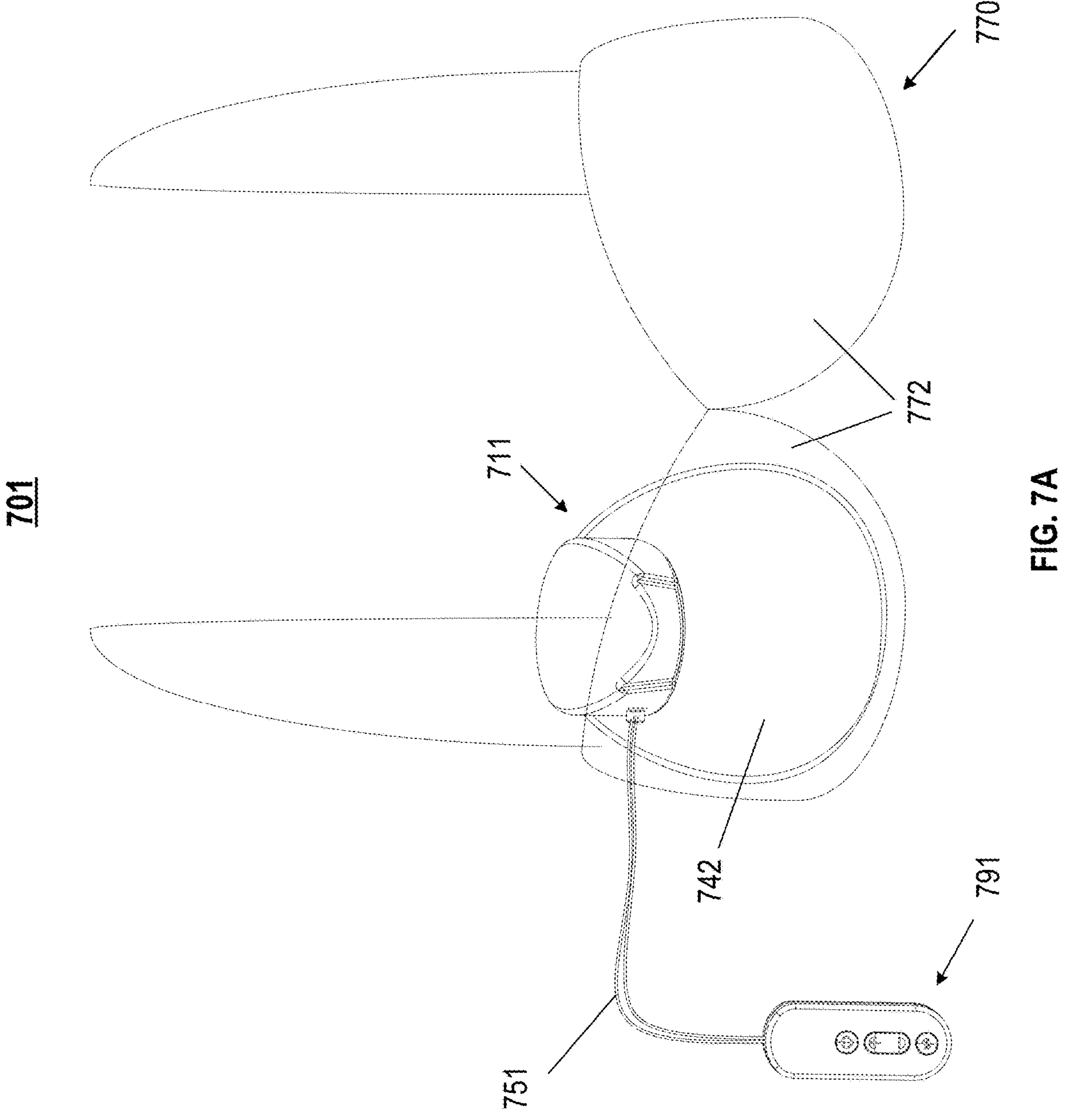
FIG. 7A illustrates an application of a breast pump device to a bra, according to some aspects of the present disclosure.

FIG. 7A illustrates an application of a breast pump device 701 to a bra 770, according to some aspects of the present disclosure. Breast pump device 701 may include a primary machine portion 711 and a secondary control portion 791, which is the same as or similar to the breast pump devices described above, such as breast pump device 400. Primary machine portion 711 and secondary control portion 791 may be the same as or similar to primary machine portion 410 and secondary control portion 490, respectively. Thus, details of the configurations and functions of breast pump device 701, primary machine portion 711, and secondary control portion 701 will not be repeated herein. Bra 770 may have a pair of breast cups 772. As shown in FIG. 7A, primary machine portion 711 may be disposed at least partially inside one of breast cups 772, while secondary control portion 791 is provided away from primary machine portion 711. Primary machine portion 711 may be connected with secondary control portion 791 via a wire 751. Wire 751 has a small size and light weight, and because it does not provide an airway, wire 751 does not malfunction when it is bent or rolled up. Alternatively, primary machine portion 711 and secondary control portion 791 can be wirelessly connected, thus making primary machine portion 711 easy to be concealed under the clothes of the user and reducing awkwardness of nursing mothers who wear breast pump device 701 in public.

Figure 7B:
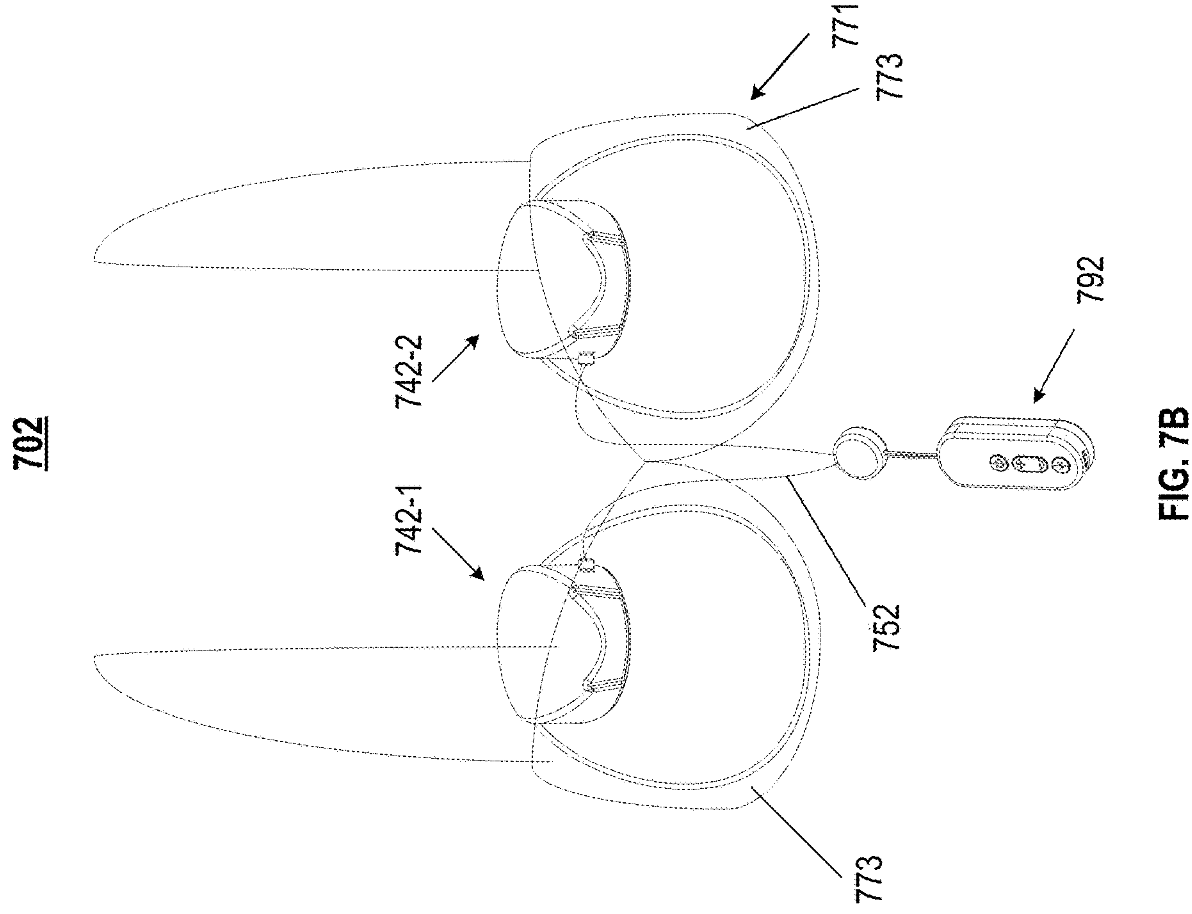
FIG. 7B illustrates an application of a breast pump system to a bra, according to some aspects of the present disclosure.

FIG. 7B illustrates an application of a breast pump system 702 to a bra 771, according to some aspects of the present disclosure. Breast pump system 702 may include two primary machine portions 742-1, 742-2 and one secondary control portion 792, which is the same as or similar to breast pump systems described above, such as breast pump system 600. Primary machine portions 742-1, 742-2 and secondary control portion 792 may be the same as or similar to primary machine portions 610-1, 610-2 and secondary control portion 690, respectively. Thus, details of the configurations and functions of breast pump system 702, primary machine portions 742-1, 742-2, and secondary control portion 792 will not be repeated herein. Bra 771 may have a pair of breast cups 773. As shown in FIG. 7B, each of primary machine portions 742-1, 742-2 may be disposed at least partially inside one of breast cups 773, while secondary control portion 792 is provided away from primary machine portions 742-1, 742-2. Primary machine portions 742-1, 742-2 may be connected with secondary control portion 792 via a wire 752. Similar to wire 751, wire 752 has a small size and light weight, and because it does not provide an airway, wire 752 does not malfunction when it is bent or rolled up. Alternatively, primary machine portions 742-1, 742-2 and secondary control portion 792 can be wirelessly connected, thus making primary machine portions 742-1, 742-2 easy to be concealed under the clothes of the user and reducing awkwardness of nursing mothers who wear breast pump system 702 in public.

Figure 7C:
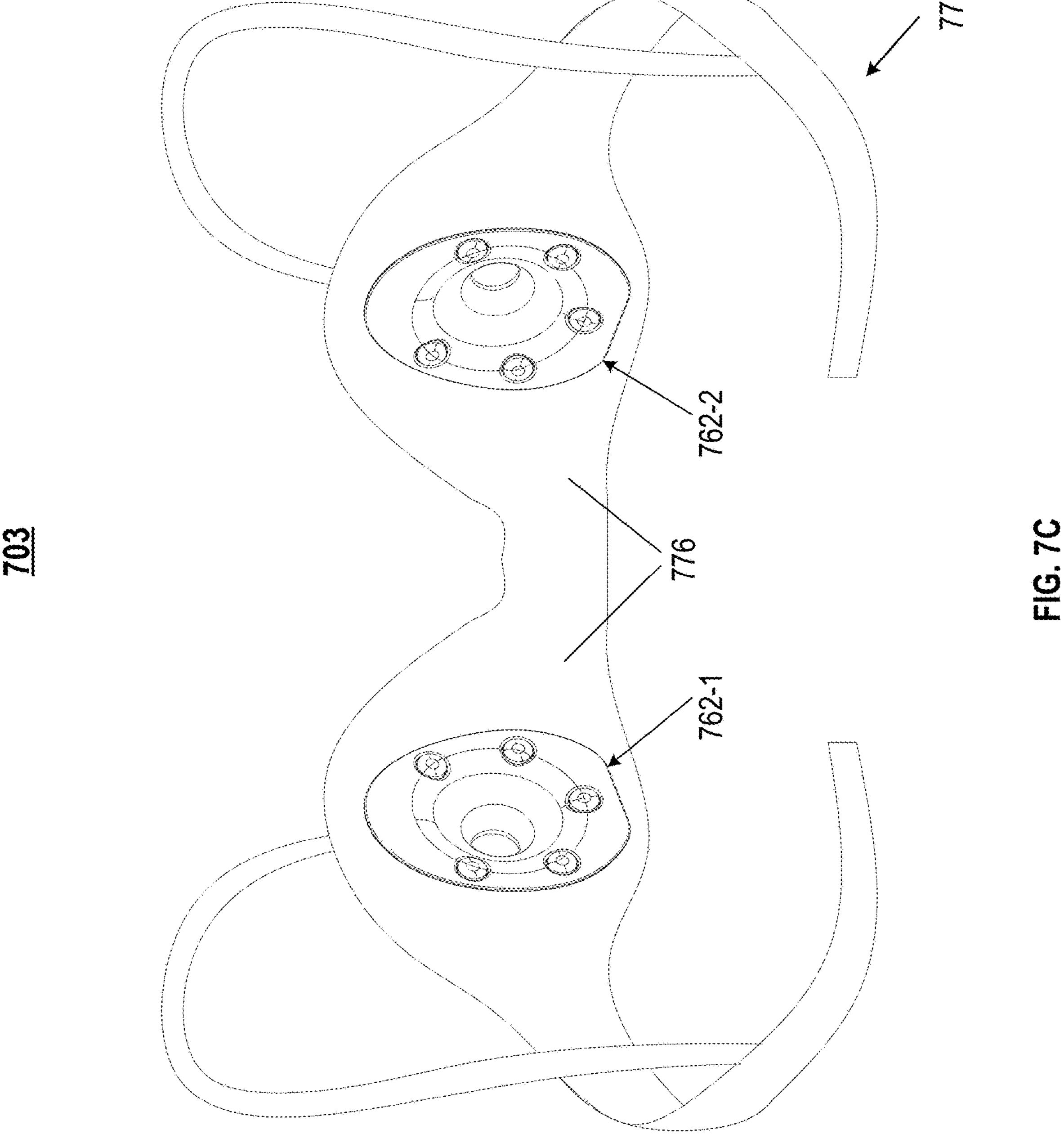
FIG. 7C illustrates a back perspective view of an in-bra breast pump system, according to some aspects of the present disclosure.

FIG. 7C illustrates a back perspective view of an in-bra breast pump system 703, according to some aspects of the present disclosure. Breast pump system 703 may include two primary machine portions 762-1, 762-2, one secondary control portion (not shown), and a bra 775. Primary machine portions 762-1, 762-2 may be the same as or similar to primary machine portions 610-1, 610-2 described above, and thus details of the configurations and functions thereof will not be repeated herein. As shown in FIG. 7B, primary machine portions 762-1, 762-2 may be integrated into two breast cups 776 of bra 775. Breast cups 776 may be designed to have the same contour as that of primary machine portions 762-1, 762-2 so that they can be fitted together with little or no room in between, thus reducing a size of in-bra breast pump system 703. The side of the breast flange of each of primary machine portions 762-1, 762-2 is exposed in order to accommodate a breast of the user. The integration of primary machine portions into a bra alleviates a nursing mother's burden of constantly monitoring the positions of standalone breast pump devices or breast pump systems in relation to the bra she is wearing.

Figure 8:
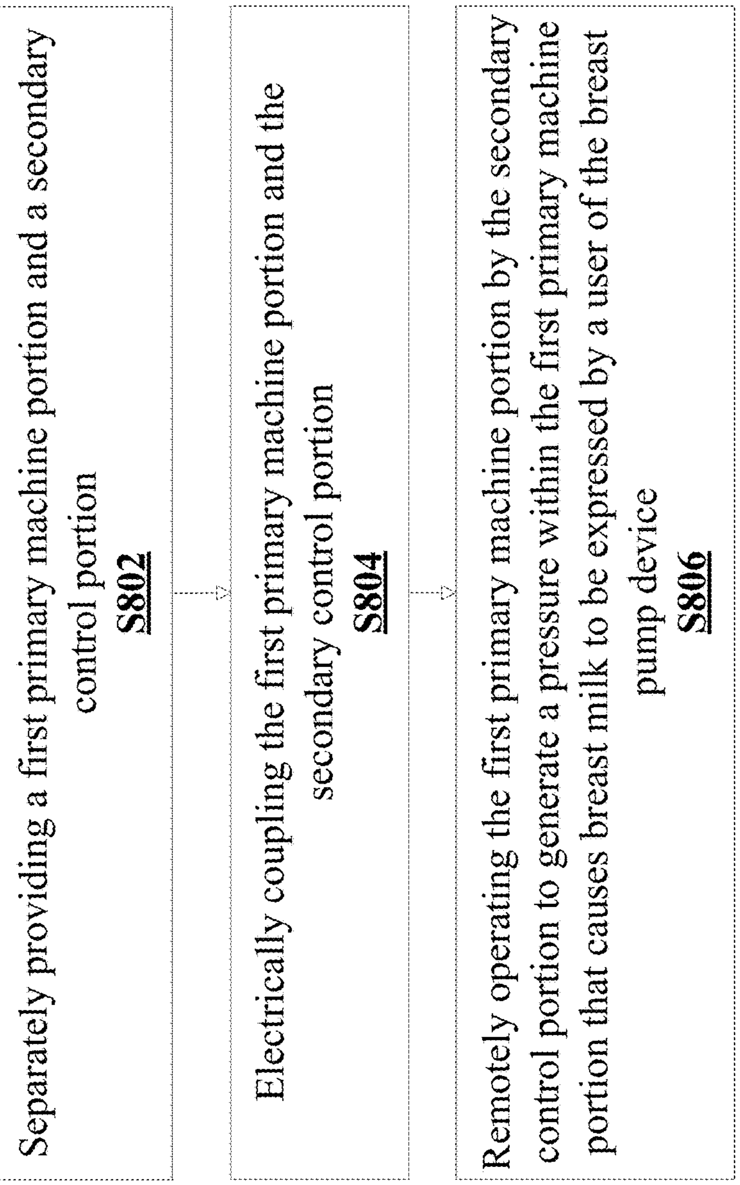
FIG. 8 illustrates a flowchart of a method for operating a breast pump device, according to some aspects of the present disclosure.

FIG. 8 illustrates a flowchart of a method 800 for operating a breast pump device, according to some aspects of the present disclosure. It is understood that the steps shown in method 800 are not exhaustive and that other steps can be performed as well before, after, or between any of the illustrated steps. Furthermore, some of the steps may be performed simultaneously, or in a different order than that shown in FIG. 8. Examples of the breast pump device in FIG. 8 may refer to the breast pump devices 100, 400, 501, 502, 503, 504, 505, 600, 600', 701, 702, and 703 described hereinabove, which, according to Step 800 (a pre-operation step), may include a primary machine portion (such as primary machine portion 110, 210, 410, 511, 512, 513, 514, 515, 610-1, 610-2, 610'-1, 610'-2, 711, 712, and 713 described hereinabove), and a secondary control portion (such as primary machine portion 190, 290, 490, 591, 592, 593, 594, 595, 690, 690', 791, and 792 described hereinabove).

Referring to FIG. 8, at step 802, a first primary machine portion and a secondary control portion are separately provided. The first primary machine portion may include a main housing, a pump attached to the main housing, and a milk container. In some embodiments, the first primary machine portion includes a communication interface that transmits or receives at least one of data or power between the first primary machine portion and the secondary control portion in wired or wireless settings. The first primary machine portion may further include a power source. The secondary control portion may include a minor housing, an input unit, a controller, a communication interface, and a power source.

At step 804, the first primary machine portion and the secondary control portion are electrically coupled. The electrical coupling dispenses the need for an airway between the two portions, thus making it easy to store the breast pump device, whether the two portions are wired or not. The electrical coupling facilitates exchange of data, power, or both between the two portions. Therefore, the first primary machine portion can function normally even without a power source provided therein, because the second control portion can supply power to the first primary machine portion via the electrical coupling. The electrical coupling can be achieved in wired or wireless settings, which has already been discussed in detail hereinabove, and thus will not be repeated herein.

At step 806, the secondary control portion remotely operates the first primary machine portion to generate a pressure within the first primary machine portion that causes a user of the breast pump device to express breast milk. In some embodiments, the user can adjust the operation modes of the pump of the first primary machine portion by changing input on the side of the secondary control portion, which is transmitted from the secondary control portion to the first primary machine portion in the form of electrical signals. In some embodiments, electric power is supplied from the secondary control portion to the first primary machine portion. In some embodiments, electric power is supplied from the first primary machine portion to the secondary control portion.

In some embodiments, the secondary control portion may be integrated into one or more consumer devices, thus being able to provide various additional functions, such as massage, music, voice control, time tracking, etc.

In some embodiments, a second primary machine portion may be provided separately from both the first primary machine portion and the secondary control portion. In some embodiments, the second primary machine portion may be electrically coupled to the secondary control portion. In some other embodiments, the second primary machine portion may be coupled to the first primary machine portion via an airway. The secondary control portion remotely operates the second primary machine portion to generate a pressure within the first primary machine portion that causes the user of the breast pump device to express breast milk.

In some embodiments, data indicating operation status of one of the primary machine portions is transmitted to the other of the primary machine portions. Operation status of the other primary machine portion is adjusted based on the transmitted data. The operation status includes at least one of in-operation, hibernation, power-off, an operation mode, operation intensity, or a circulation period.

The foregoing description of the specific implementations will so reveal the general nature of the present disclosure that others can, by applying knowledge within the skill of the art, readily modify and/or adapt for various applications of such specific implementations, without undue experimentation, and without departing from the general concept of the present disclosure. Therefore, such adaptations and modifications are intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Implementations of the present disclosure have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The Summary and Abstract sections may set forth one or more but not all exemplary implementations of the present disclosure, and thus, are not intended to limit the present disclosure and the appended claims in any way.

The breadth and scope of the present disclosure should not be limited by any of the above-described exemplary implementations, but should be defined only in accordance with the following claims and their equivalents.

What is claimed is:

1. A breast pump device, comprising:

a primary machine portion; and a secondary control portion without any pump, the secondary control portion being provided separately from the primary machine portion, wherein the primary machine portion comprises:

a main housing;

a pump attached to the main housing and configured to generate a pressure to cause breast milk to be expressed by a user of the breast pump device; and a milk container coupled to the pump and configured to accommodate the breast milk, wherein the secondary control portion is electrically coupled to the primary machine portion and configured to remotely operate the primary machine portion, wherein the primary machine portion comprises a power source configured to supply electrical power to the secondary control portion, and wherein the primary machine portion is configured to be worn on a breast of the user during operation, and the secondary control portion is integrated into a wearable device configured to be worn on the neck or head of the user.

2. The breast pump device of claim 1, wherein the secondary control portion is connected to the primary machine portion by wire.

3. The breast pump device of claim 2, wherein the wire is detachable from at least one of the primary machine portion and the secondary control portion.

4. The breast pump device of claim 1, wherein the secondary control portion comprises a power source configured to supply electrical power to one or both of the secondary control portion and the primary machine portion.

5. The breast pump device of claim 1, wherein the wearable device is one of the following: a headphone, a massager, a neck-hanging device, or an ear-hook headset.

6. The breast pump device of claim 1, wherein the secondary control portion is configured to remotely operate the pump by controlling at least one of turning on the pump, turning off the pump, switching a mode, adjusting pumping intensity, adjusting massage intensity, or setting a circulation period.

7. A breast pump system comprising two primary machine portions, wherein at least one of the primary machine portions comprises:

a main housing, a pump attached to the main housing and configured to generate a pressure to cause breast milk to be expressed by a user of the breast pump system, and a milk container coupled to the pump and configured to accommodate the breast milk;

wherein the breast pump system further comprises a secondary control portion provided separately from the two primary machine portions;

wherein the secondary control portion is electrically coupled to at least one primary machine portion by wire and configured to remotely operate the two primary machine portions;

wherein at least one of the primary machine portions comprises a power source configured to supply electrical power to the secondary control portion; and wherein the two primary machine portions are each configured to be worn on a breast of the user during operation, and the secondary control portion is configured to be worn on the neck or head of the user.

8. The breast pump system of claim 7, wherein the secondary control portion is configured to operate either of the two primary machine portions independently from its operation of the other.

9. The breast pump system of claim 7, wherein the two primary machine portions are configured to transmit data indicating operation status of the two primary machine portions between each other.

10. The breast pump system of claim 9, wherein one of the two primary machine portions is configured to adjust operation status based on the data indicating the operation status of the other primary machine portion.

11. The breast pump system of claim 9, wherein the operation status comprises at least one of in-operation, hibernation, power-off, operation mode, operation intensity, or circulation period.

12. The breast pump system of claim 7, wherein the secondary control portion is electrically coupled to a first primary machine portion, and the first primary machine portion is connected to a second primary machine portion by an airway.

13. The breast pump system of claim 12, wherein the second primary machine portion does not have any pump, and the pump of the first primary machine portion provides pumping operations to the second primary machine portion in order to cause the user to express milk.

14. The breast pump system of claim 7, further comprising a bra with at least one breast cup, wherein at least one of the two primary machine portions is integrated into the at least one breast cup.

15. A method for operating a breast pump device having a first primary machine portion and a secondary control portion, comprising:

separately providing the first primary machine portion and the secondary control portion;

electrically coupling the first primary machine portion and the secondary control portion by wire;

remotely operating the first primary machine portion by the secondary control portion to generate a pressure within the first primary machine portion that causes breast milk to be expressed by a user of the breast pump device;

supplying electrical power from the first primary machine portion to the secondary control portion, wherein the primary machine portion is worn on a breast of the user during operation, and the secondary control portion is worn on the neck or head of the user.

16. The method of claim 15, further comprising:

supplying electrical power from the secondary control portion to the first primary machine portion.

17. The method of claim 15, wherein the breast pump device comprises a second primary machine portion, and the method further comprising:

providing the second primary machine portion separately from the first primary machine portion and the secondary control portion;

electrically coupling the second primary machine portion to the secondary control portion; and remotely operating the second primary machine portion by the secondary control portion to generate a pressure within the second primary machine portion that causes the user of the breast pump device to express breast milk.

18. The method of claim 17, further comprising:

transmitting data indicating operation status of one of the first and second primary machine portions to the other; and adjusting operation status of the other of the first and second primary machine portions based on the transmitted data.

19. The method of claim 15, wherein the breast pump device comprises a second primary machine portion, and the method further comprising:

providing the second primary machine portion separately from the first primary machine portion and the secondary control portion;

coupling the second primary machine portion to the first primary machine portion via an airway; and remotely operating the second primary machine portion by the secondary control portion to generate a pressure, through the pump of the first primary machine portion, within the second primary machine portion that causes the user of the breast pump device to express breast milk.

* * * * *